United States Patent
Lee et al.

(10) Patent No.: US 10,267,737 B2
(45) Date of Patent: Apr. 23, 2019

(54) NEAR-INFRARED FLUORESCENT PROBE FOR DETECTING ALKALINE PHOSPHATASE AND MANUFACTURING METHOD THEREOF

(71) Applicant: KOREA RESEARCH INSTITUTE OF BIOSCIENCE AND BIOTECHNOLOGY, Daejeon (KR)

(72) Inventors: Chang-Soo Lee, Daejeon (KR); Chul Soon Park, Daejeon (KR); Oh Seok Kwon, Daejeon (KR); Tai Hwan Ha, Daejeon (KR)

(73) Assignee: KOREA RESEARCH INSTITUTE OF BIOSCIENCE AND BIOTECHNOLOGY, Daejeon (KR)

( * ) Notice: Subject to any disclaimer, the term of this patent is extended or adjusted under 35 U.S.C. 154(b) by 0 days.

(21) Appl. No.: 15/824,157

(22) Filed: Nov. 28, 2017

(65) Prior Publication Data
US 2018/0149596 A1     May 31, 2018

(30) Foreign Application Priority Data

Nov. 30, 2016   (KR) .................. 10-2016-0162235
Apr. 5, 2017    (KR) .................. 10-2017-0044300

(51) Int. Cl.
| | | |
|---|---|---|
| *C07F 9/06* | (2006.01) |
| *G01N 21/64* | (2006.01) |
| *C12N 9/18* | (2006.01) |
| *C07D 209/10* | (2006.01) |
| *C07D 311/80* | (2006.01) |
| *C09K 11/06* | (2006.01) |

(52) U.S. Cl.
CPC ....... *G01N 21/6486* (2013.01); *C07D 209/10* (2013.01); *C07D 311/80* (2013.01); *C09K 11/06* (2013.01); *C12N 9/18* (2013.01); *C12Y 301/03001* (2013.01); *C09K 2211/1007* (2013.01); *C09K 2211/1029* (2013.01); *C09K 2211/1088* (2013.01)

(58) Field of Classification Search
CPC .......... C07F 9/06; C07F 9/062; G01N 21/64; C12Y 301/03001; C12N 9/18
See application file for complete search history.

(56) References Cited

PUBLICATIONS

Chemical Abstracts Registry No. 2133510-45-7, indexed in the Registry file on STN CAS Online Oct. 11, 2017. (Year: 2017).*
Chemical Abstracts Registry No. 2133510-46-8, indexed in the Registry file on Stn Cas Online Oct. 11, 2017. (Year: 2017).*
M. Syakalima et al., "The canine alkaline phosphatases : A review of the isoenzymes in serum, analytical methods and their diagnostic application", Japanese Journal of Veterinary Research, vol. 46(1), pp. 3-11, 1998.
J. E. Coleman, "Structure and Mechanism of Alkaline Phosphatase", Annu. Rev. Biophys. Biomol. Stuct., vol. 21, p. 441-483, 1992.
N. J. Fernandez and B. A. Kidney, "Alkaline phosphatase: beyond the liver", Veterinary Clinical Pathology, vol. 36(3), pp. 223-233, 2007.
D. Goltzman and D. Miao, "Alkaline Phosphatase", Encyclopedia Endocr. Dis., vol. 1, p. 164, 2004.
K. Ooi et al., "High-Molecular Intestinal Alkaline Phosphatase in Chronic Liver Diseases", Journal of Clinical Laboratory Analysis, vol. 21, pp. 133-139, 2007.
P. L. Wolf, "Clinical Significance of Serum High-Molecular-Mass Alkaline Phosphatase, Alkaline Phosphatase-Lipoprotein-X Complex, and Intestinal Variant Alkaline Phosphatase", Journal of Clinical Laboratory Analysis, vol. 8, pp. 172-176, 1994.
Róbert E. Gyurcsányi et al., "Amperometric microcells for alkaline phosphatase assay", Analyst, vol. 127, pp. 235-240, 2002.

* cited by examiner

*Primary Examiner* — Laura L Stockton
(74) *Attorney, Agent, or Firm* — The PL Law Group, PLLC

(57) ABSTRACT

A near-infrared fluorescent probe for detecting ALP is represented by Chemical 1. The fluorescent probe capable of detecting ALP can selectively detect ALP only quickly and accurately. In addition, the fluorescent probe allows monitoring of a biological phenomenon occurring in cells and tissues through noninvasive in-vivo imaging and during the early osteogenic differentiation in real time.

13 Claims, 34 Drawing Sheets

NEAR-INFRARED FLUORESCENT PROBE FOR DETECTING ALKALINE PHOSPHATASE AND MANUFACTURING METHOD THEREOF

CROSS-REFERENCE TO RELATED APPLICATIONS

This application claims, under 35 U.S.C. § 119, the priority of Korean Patent Application No. 10-2016-0162235, filed on Nov. 30, 2016, and Korean Patent Application No. 10-2017-0044300, filed on Apr. 5, 2017, in the Korean Intellectual Property Office, the disclosure of which is incorporated herein by reference in its entirety.

BACKGROUND

1. Technical Field

The present disclosure relates to a near-infrared fluorescent probe for detecting alkaline phosphatase (ALP) and a method for preparing the same.

2. Background Art

Alkaline phosphatases (hereinafter referred to as 'ALPs'), which catalyze the hydrolysis and transphosphorylation of a wide variety of monophosphate esters, consist of a group of isoenzymes that are widespread in mammalian tissues (M. Syakalima et al., *Jpn. J. Vet. Res.*, 1998, 46: 3; J. E. Coleman, *Annu. Rev. Biophys. Biomol. Struct.*, 1992, 21: 441). The human genome encodes four different ALP enzyme isoforms, namely, tissue specific ALPs (intestinal, placental and germ cell ALPs) and tissue non-specific ALPs, which are expressed in most tissues including the liver, bone and kidney (N. J. Fermandez and B. A. Kidney, *Vet. Clin. Pathol.*, 2007, 36: 223).

Serum ALP activity is routinely used as a diagnostic indicator of many human diseases, including bone diseases (osteoblastic bone cancer, Paget's disease and osteomalacia) and liver diseases (cancer, hepatitis and obstructive jaundice) (D. Goltzman and D. Miao, *Encyclopedia Endocr. Dis.*, 2004, 1: 164; K. Ooi et al., *J. Clin. Lab. Anal.*, 2007, 21: 133; P. L. Wolf, *J. Clin. Lab. Anal.*, 1994, 8: 172; R. E. Gyurcsanyi et al., *Analyst*, 2002, 127: 235.).

Despite the extensive studies on ALP, its diverse physiological and pathological functions have not been fully elucidated. It is only recently that the pivotal biological roles of ALP in the maintenance of intestinal homeostasis and protection have begun to be revealed. Moreover, detailed mechanisms of ALP activity regulation during pathogenesis still remain unanswered. This is in part a consequence of the absence of an appropriate probe for real-time tracking of ALP activity in living systems. Therefore, the development of a sensitive and biocompatible probe with suitable intracellular localization is highly desirable for the study of ALP.

SUMMARY

The present disclosure is directed to providing a fluorescent probe capable of detecting ALP through noninvasive in-vivo imaging and a method for preparing the same.

The present disclosure is also directed to providing a bone scaffold using a fluorescent probe for detecting ALP.

In an aspect, the present disclosure provides a fluorescent probe for detecting ALP, represented by Chemical Formula 1:

[Chemical Formula 1]

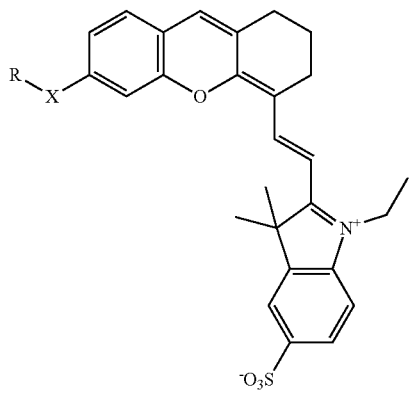

wherein X is O or NH, and R is

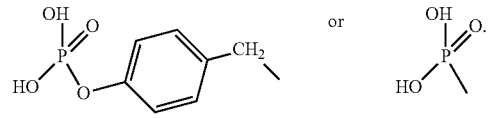

The fluorescent probe may fluoresce at 650-750 nm by reacting with ALP in vivo.

The fluorescent probe may be represented by Chemical Formula 2:

[Chemical Formula 2]

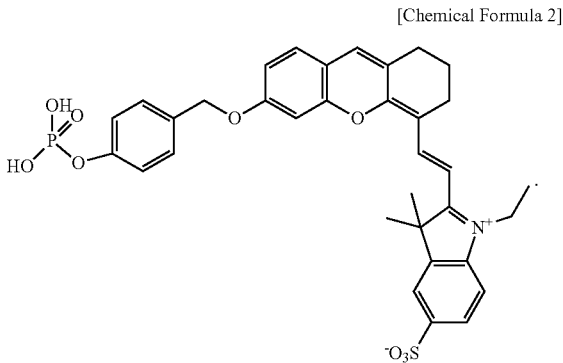

Also, the fluorescent probe may be represented by Chemical Formula 3:

[Chemical Formula 3]

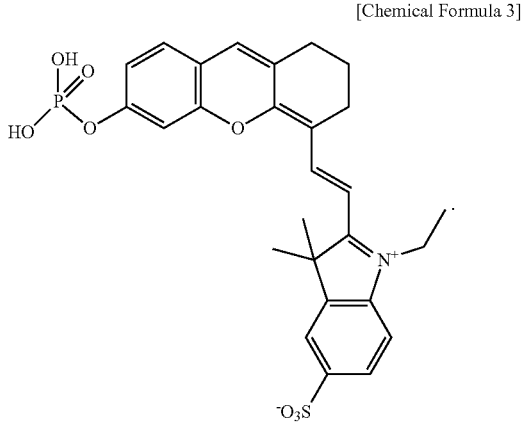

In another aspect, the present disclosure provides a method for preparing a fluorescent probe for detecting ALP, including: a step of obtaining a compound represented by Chemical Formula 6 by reacting a compound represented by Chemical Formula 4 with a compound represented by Chemical Formula 5; a step of obtaining a compound represented by Chemical Formula 8 by reacting the compound represented by Chemical Formula 6 with a compound represented by Chemical Formula 7; and a step of obtaining a compound represented by Chemical Formula 2 by reacting the compound represented by Chemical Formula 8 with a silane compound:

[Chemical Formula 4]

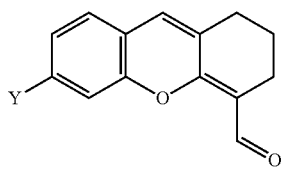

wherein Y is OH or NH₂

[Chemical Formula 5]

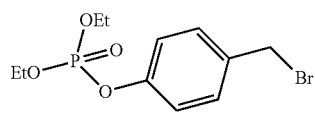

[Chemical Formula 6]

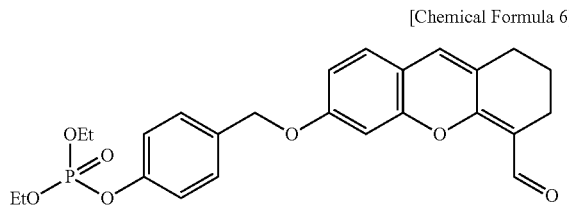

[Chemical Formula 7]

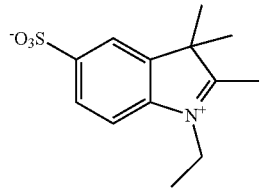

[Chemical Formula 8]

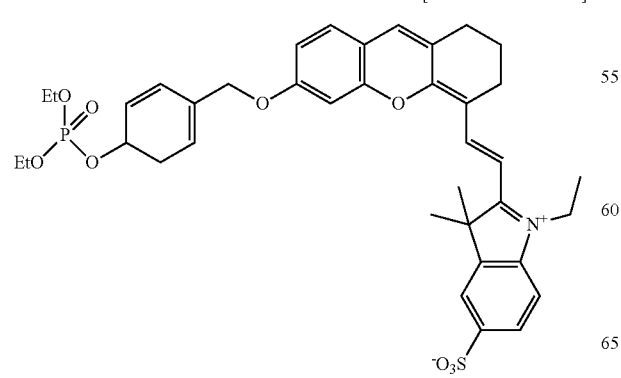

-continued

[Chemical Formula 2]

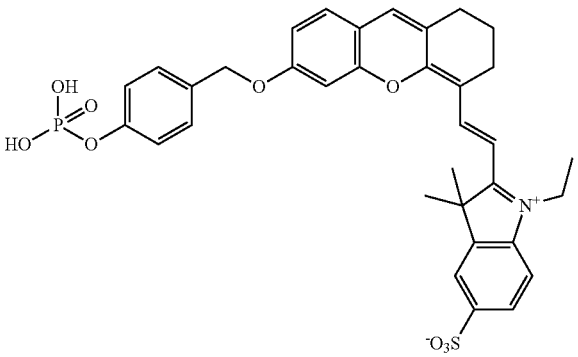

In another aspect, the present disclosure provides a method for preparing a fluorescent probe for detecting ALP, including: a step of obtaining a compound represented by Chemical Formula 10 by reacting a compound represented by Chemical Formula 4 with a compound represented by Chemical Formula 9; a step of obtaining a compound represented by Chemical Formula 11 by reacting the compound represented by Chemical Formula 10 with a compound represented by Chemical Formula 7; and a step of obtaining a compound represented by Chemical Formula 3 by reacting the compound represented by Chemical Formula 11 with a silane compound:

[Chemical Formula 4]

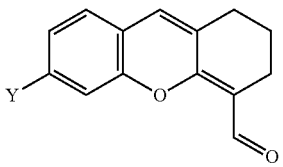

wherein Y is OH or NH₂

[Chemical Formula 9]

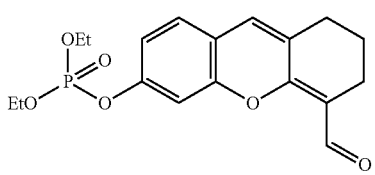

[Chemical Formula 10]

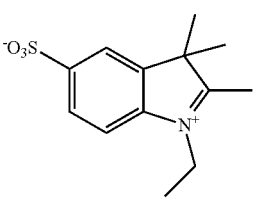

[Chemical Formula 7]

-continued

[Chemical Formula 11]

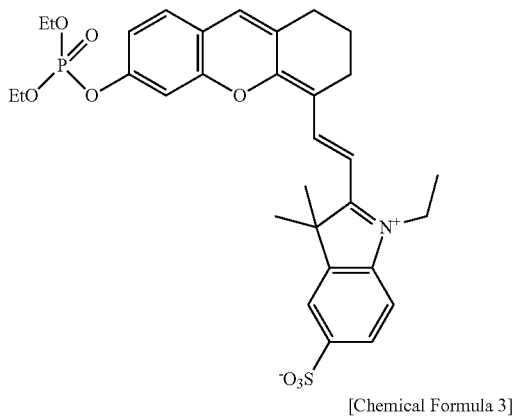

[Chemical Formula 3]

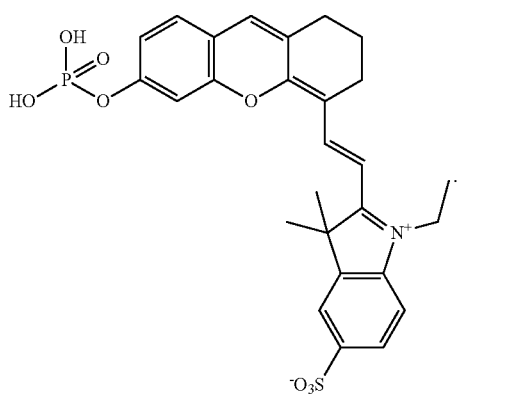

The silane compound may be iodotrimethylsilane (Me$_3$SiI).

In another aspect, the present disclosure provides a bone scaffold including the fluorescent probe for detecting ALP according to the present disclosure.

The fluorescent probe capable of detecting ALP according to an embodiment of the present disclosure can selectively detect ALP only quickly and accurately.

In addition, it allows monitoring of a biological phenomenon occurring in cells and tissues through noninvasive in-vivo imaging.

DETAILED DESCRIPTION

Hereinafter, exemplary embodiments of the present disclosure will be described in detail with reference to the accompanying drawings. Prior to the description, it should be understood that the terms used in the specification and the appended claims should not be construed as limited to general and dictionary meanings, but interpreted based on the meanings and concepts corresponding to technical aspects of the present disclosure on the basis of the principle that the inventor is allowed to define terms appropriately for the best explanation. Therefore, the description proposed herein is just an exemplary example for the purpose of illustrations only, not intended to limit the scope of the disclosure, so it should be understood that other equivalents and modifications can be made thereto without departing from the scope of the disclosure.

An embodiment of the present disclosure provides a fluorescent probe for detecting ALP, represented by Chemical Formula 1:

[Chemical Formula 1]

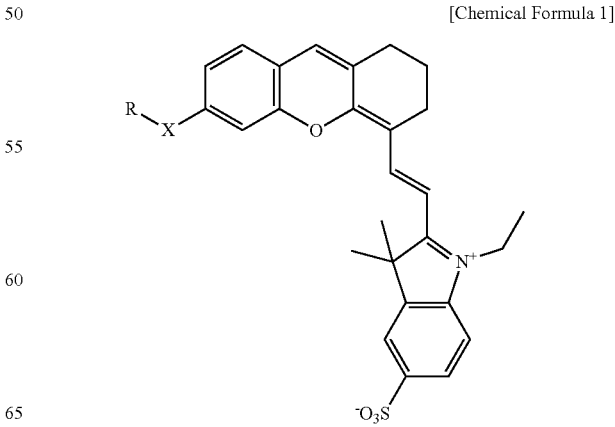

wherein X is O or NH; and
R is

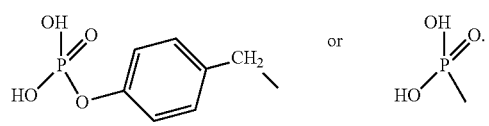

The phosphate group (—PO$_4$) included in the R may improve accessibility to a scaffold containing bone components.

And, the sulfonate group included in the compound may allow for effective detection of ALP contained in an aqueous medium or a living organism due to superior water solubility and biocompatibility.

As a specific example, the compound may be represented by Chemical Formula 2.

[Chemical Formula 2]

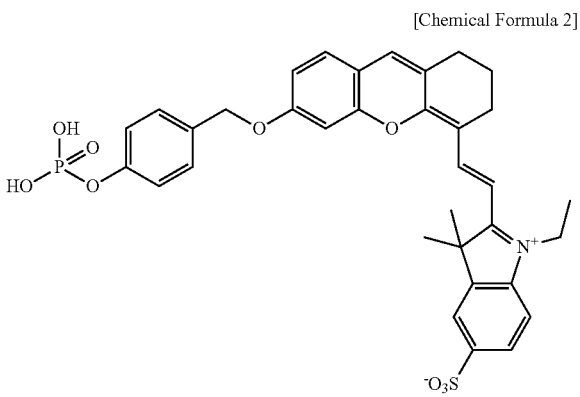

As another specific example, the compound may be represented by Chemical Formula 3.

[Chemical Formula 3]

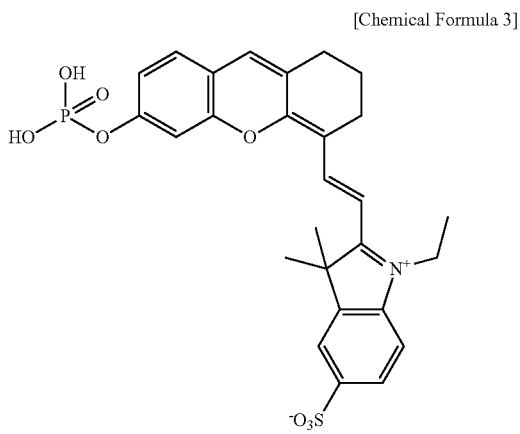

Figure 1:
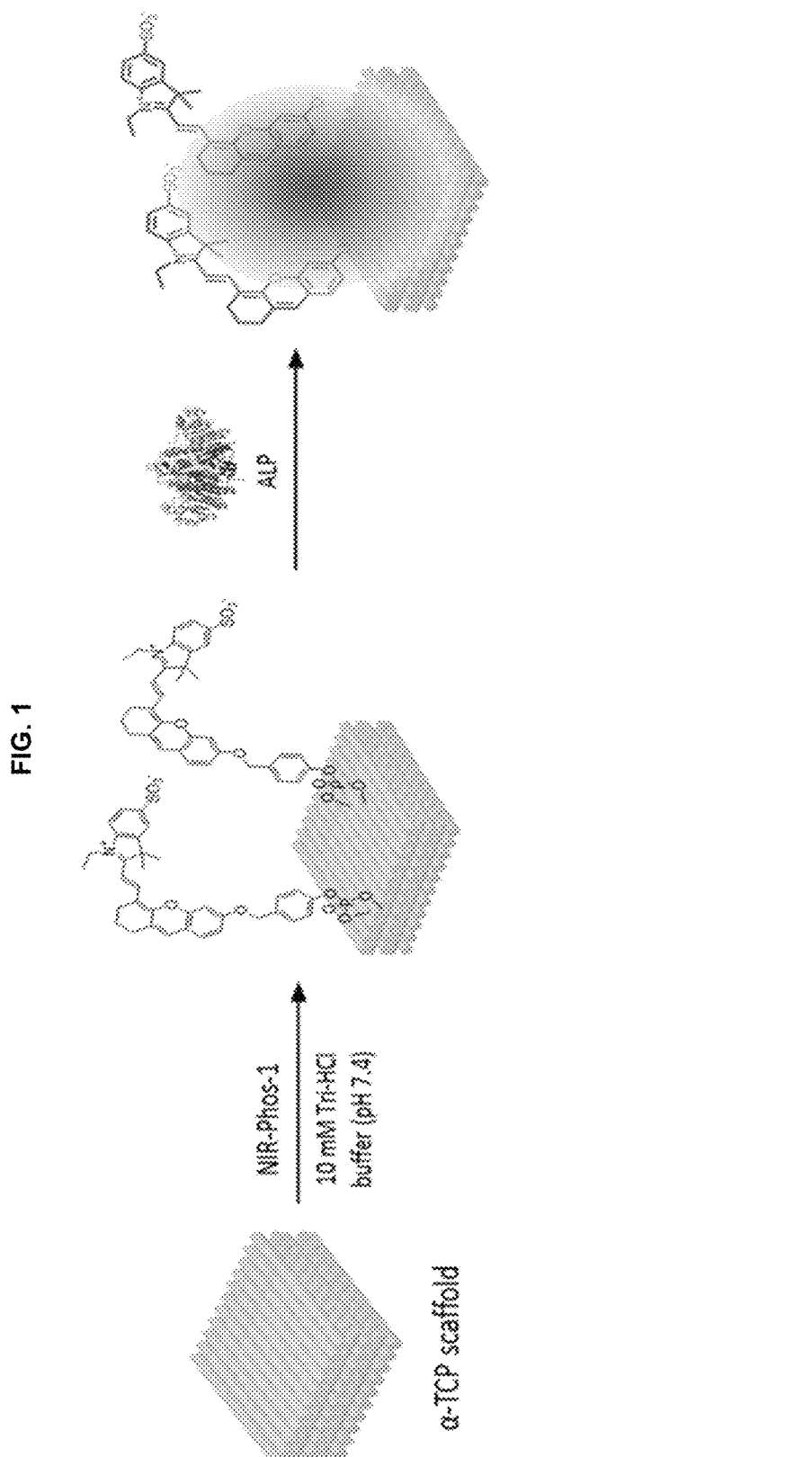
FIG. 1 shows a reaction between a fluorescent probe according to an embodiment of the present disclosure and ALP.

The fluorescent probe for detecting ALP of an embodiment of the present disclosure provides a fluorescence signal as dephosphorylation occurs due to hydrolysis of ALP, through excited state intramolecular proton transfer (ESIPT) (see FIG. 1).

The fluorescent probe for detecting ALP is a near-infrared fluorescent (NIRF) material and exhibits fluorescence at wavelengths of 650-750 nm when to injected into a living organism. Therefore, ALP can be detected by measuring the fluorescence.

In addition, because the fluorescent probe for detecting ALP has a limit of detection (LOD) of $10^{-5}$-$10^{-3}$ UmL$^{-1}$, which can be observed by fluorescence imaging, it can be used to quantify ALP activity in a range of 0-1.0 UmL$^{-1}$. As a specific example, the fluorescent probe for detecting ALP of an embodiment of the present disclosure can display fluorescence response to 0.1 UmL$^{-1}$ ALP within 1.5 minutes after addition.

The compound represented by Chemical Formula 2 according to an embodiment of the present disclosure may be prepared by a method including:

a step of obtaining a compound represented by Chemical Formula 6 by reacting a compound represented by Chemical Formula 4 with a compound represented by Chemical Formula 5;

a step of obtaining a compound represented by Chemical Formula 8 by reacting the compound represented by Chemical Formula 6 with a compound represented by Chemical Formula 7; and a step of obtaining a compound represented by Chemical Formula 2 by reacting the compound represented by Chemical Formula 8 with a silane compound:

[Chemical Formula 4]

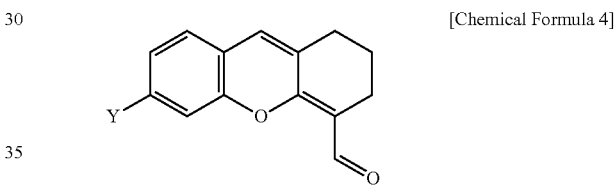

wherein Y is OH or NH$_2$

[Chemical Formula 5]

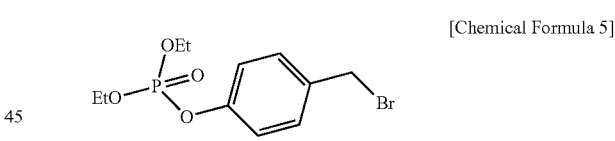

[Chemical Formula 6]

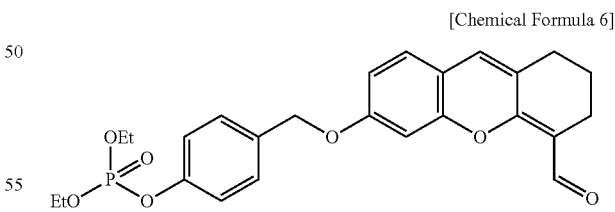

[Chemical Formula 7]

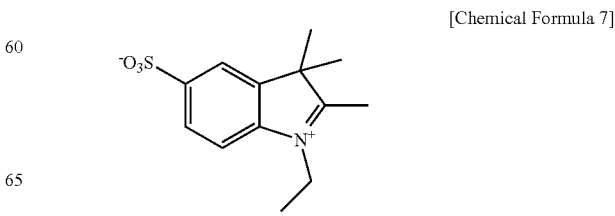

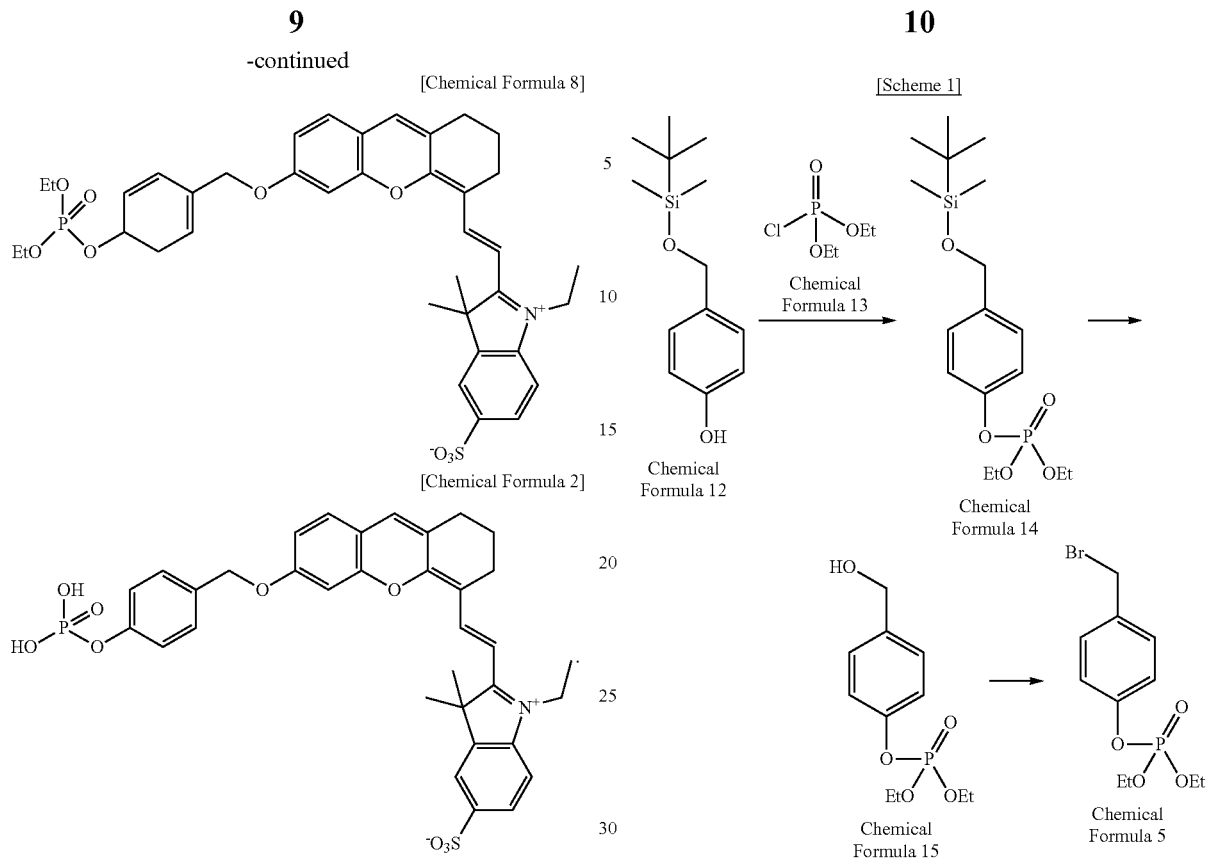

Hereinafter, the method for preparing the compound represented by Chemical Formula 2 is described in detail.

First, a compound represented by Chemical Formula 6 may be produced by dissolving a compound represented by Chemical Formula 4 and a compound represented by Chemical Formula 5 together with $Cs_2CO_3$ in dimethylformamide (hereinafter referred to as DMF).

And, a compound represented by Chemical Formula 8 may be produced to by reacting the compound represented by Chemical Formula 6 with a compound represented by Chemical Formula 7 (1-ethyl-2,3,3-trimethyl-3H-indol-1-ium-5-sulfonate) at 40-50° C.

Finally, the compound represented by Chemical Formula 8 is dissolved in dichloromethane (hereinafter referred to as DCM) and then mixed with iodotrimethylsilane ($Me_3Sil$) as a silane compound through stirring. Then, after a predetermined time, the compound represented by Chemical Formula 2 may be prepared by removing the solvent from the mixture and then adding methanol (MeOH).

The compound represented by Chemical Formula 5 used in the method for preparing the compound represented by Chemical Formula 2 may be prepared by Scheme 1 as described below.

Scheme 1 includes: a step of obtaining a compound represented by Chemical Formula 14 by reacting a compound represented by Chemical Formula 12 with a compound represented by Chemical Formula 13; a step of obtaining a compound represented by Chemical Formula 15 using the compound represented by Chemical Formula 14; and a step of obtaining the compound represented by Chemical Formula 5 by reacting the compound represented by Chemical Formula 15 with a bromine compound.

Hereinafter, the method for preparing the compound represented by Chemical Formula 5 is described in detail.

First, the compound represented by Chemical Formula 14 may be produced by mixing the compound represented by Chemical Formula 12 and the compound represented by Chemical Formula 13 in an organic solvent by stirring, drying the mixture and then concentrating the same under reduced pressure. Although the organic solvent is not specially limited, trimethylamine (TEA) may be used specifically.

The compound represented by Chemical Formula 15 may be produced by mixing the compound represented by Chemical Formula 14 with an alcohol and hydrogen chloride by stirring and then neutralizing the mixture. Finally, the compound represented by Chemical Formula 5 may be produced by mixing the compound represented by Chemical Formula 15 with a bromine compound such as carbon tetrabromide ($CBr_4$) and then adding triphenylphosphine.

The compound represented by Chemical Formula 3 according to an embodiment of the present disclosure may be prepared by a method including:

a step of obtaining a compound represented by Chemical Formula 10 by reacting a compound represented by Chemical Formula 4 with a compound represented by Chemical Formula 9;

a step of obtaining a compound represented by Chemical Formula 11 by reacting the compound represented by Chemical Formula 10 with a compound represented by Chemical Formula 7; and a step of obtaining a compound represented by Chemical Formula 3 by reacting the compound represented by Chemical Formula 11 with a silane compound:

[Chemical Formula 4]

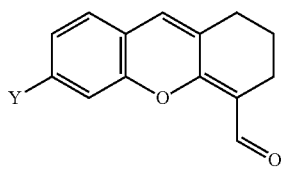

wherein Y is OH or NH$_2$

[Chemical Formula 9]

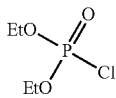

[Chemical Formula 10]

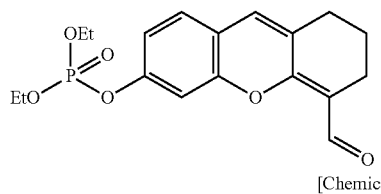

[Chemical Formula 7]

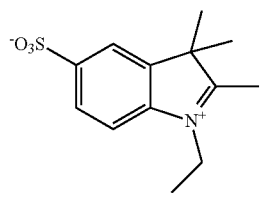

[Chemical Formula 11]

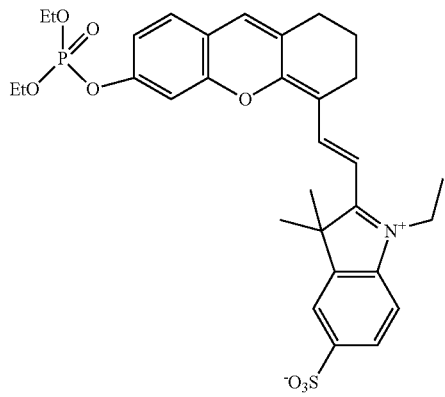

[Chemical Formula 3]

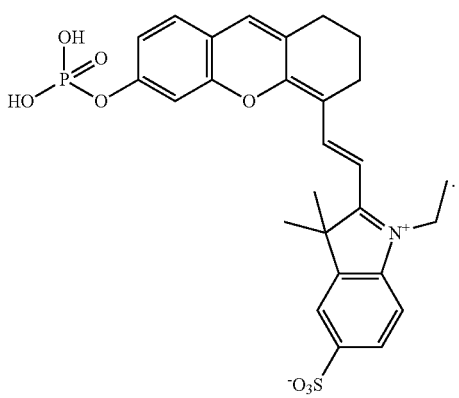

Hereinafter, the method for preparing the compound represented by Chemical Formula 3 is described in detail.

First, the compound represented by Chemical Formula 10 may be produced by dissolving the compound represented by Chemical Formula 4 and the compound represented by Chemical Formula 9 together with Cs$_2$CO$_3$ in anhydrous DMF.

The compound represented by Chemical Formula 11 may be produced by reacting the compound represented by Chemical Formula 10 with the compound represented by Chemical Formula 7 at 40-50° C.

Finally, the compound represented by Chemical Formula 3 may be prepared by dissolving the compound represented by Chemical Formula 11 in anhydrous DCM, mixing with iodotrimethylsilane (Me$_3$SiI) as a silane compound by stirring, removing the solvent from the mixture after a predetermined time, and then adding methanol (MeOH).

The fluorescent probe for detecting ALP according to an embodiment of the present disclosure may be included in a bone scaffold. The bone scaffold may be used to prevent or treat a bone disease. Specifically, it can be used for any disease occurring due to decreased bone density caused by insufficient bone formation, excessive osteoclasis due to inflammation of the joint, etc. For example, it may be used for osteoporosis, juvenile osteoporosis, osteogenesis imperfecta, osteomalacia, osteonecrosis, rickets, osteomyelitis, alveolar bone loss, Paget's disease of bone, hypercalcemia, primary hyperparathyroidism, metastatic bone disease, myeloma, bone loss in rheumatoid arthritis, bone loss caused by cancer, fibrous dysplasia of bone, adynamic bone disease, metabolic bone disease, age-related loss of bone mass, etc.

The fluorescent probe included in the bone scaffold may serve to monitor osteogenesis in real time.

While the exemplary embodiments have been shown and described, it will be understood by those of ordinary skill in the art to which the present disclosure belongs that various modifications and may be made thereto without departing from the spirit and scope of the present disclosure. Accordingly, the exemplary embodiments described in the present disclosure are not intended to limit the technical idea of the present disclosure but to describe it and the scope of the present disclosure is not limited by the exemplary embodiments. The scope of the present disclosure should be interpreted from the appended claims and it should be understood that all equivalent technical ideas fall within the scope of the present disclosure.

Hereinafter, the present disclosure will be described in more detail through examples. However, the following examples are for illustrative purposes only and it will be obvious to those of ordinary skill in the art to that the scope of the present disclosure is not limited by the scope of the examples.

EXPERIMENTAL METHODS

Silica column chromatography: MP Biomedicals, Silica 40-63, 60A.

$^1$H and $^{13}$C NMR spectroscopy: Varian UNITY INOVA, AS600 MHz NMR spectrometer.

Chemical change: ppm for residual solvent resonance.

Mass spectrometry (MS): Bruker micrOToF-QII, electrospray ionizer (ESI).

UV-vis spectroscopy: Beckman Coulter DU 800.

Fluorescence spectroscopy: Scinco FS-2 spectrometer, 37.0±0.05° C.

Synthesis Example 1. Synthesis of Compound Represented by Chemical Formula 15

Generally known 4-(((tert-butyldimethylsilyl)oxy) methyl)phenol (compound represented by Chemical Formula 12) was prepared.

Then, dichloromethane (DCM, 100 mL) was mixed with a mixture of the prepared 4-(((tert-butyldimethylsilyl)oxy) methyl)phenol (3.84 g, 16.1 mmol) and trimethylamine (TEA, 11 mL/80.5 mmol) and then diethyl chlorophosphate (5.56 g, 32.2 mmol) was added. Then, the reaction mixture was stirred overnight at room temperature under argon atmosphere. The reaction mixture was diluted with DCM (100 mL), extracted with water (2×100 mL) and then washed with brine (100 mL). Then, the organic layer was dried with $Na_2SO_4$ and concentrated under reduced pressure to obtain an oily crude product (compound represented by Chemical Formula 14). The crude product was used in the following process without further purification.

The crude product obtained above was stirred together with EtOH (100 mL). Then, after adding HCl (8 mL) at room temperature, the reaction mixture was stirred for 20 minutes and then neutralized with $NaHCO_3$. The mixture was extracted with ether (3×80 mL) and the organic layer was dried with $Na_2SO_4$, concentrated and then purified by silica column chromatography using ethyl acetate/n-hexane (volume ratio: 1/2 to 1/1) as an eluent.

The result of $^1H$ NMR and $^{13}C\{^1H\}$ NMR spectroscopy and mass spectroscopy of the finally obtained compound represented by Chemical Formula 15 (diethyl(4-(hydroxymethyl)phenyl)phosphate), 3.96 g, 94%) is as follows.

$^1H$ NMR ($CDCl_3$, 600 MHz): δ 7.32 (d, 2H, J=8.4 Hz), 7.17 (dd, 2H, J=9.0, 1.2 Hz), 4.62 (s, 2H), 4.23 (m, 4H), 1.35 (m, 6H) ppm.

$^{13}C\{^1H\}$ NMR ($CDCl_3$, 120 MHz): δ 149.90, 149.86, 138.02, 128.26, 119.89, 119.86, 64.66, 64.62, 64.29, 16.08, 16.04 ppm.

MS (m/z): Calcd. for $[MH]^+$ 261.1, found 261.1.

Synthesis Example 2. Synthesis of Compound Represented by Chemical Formula 5

Dichloromethane (DCM, 57 mL) was mixed with a mixture containing the prepared compound represented by Chemical Formula 15 (1.2 g, 4.61 mmol) and carbon tetrabromide (2.29 g, 6.92 mmol) and then triphenylphosphine (1.81 g, 6.92 mmol) was added at 0° C. Then, the reaction mixture was stirred at room temperature for 7 hours.

After removing the solvent by evaporating, the reaction mixture was purified by silica column chromatography using ethyl acetate/n-hexane (volume ratio: 1/2 to 1/1) as an eluent.

The result of $^1H$ NMR and $^{13}C\{^1H\}$ NMR spectroscopy and mass spectroscopy of the finally obtained compound represented by Chemical Formula 5 ((4-(bromomethyl)phenyl diethyl phosphate), 1.3 g, 87%) is as follows.

$^1H$ NMR ($CDCl_3$, 600 MHz): δ 7.38 (d, 2H, J=9.0 Hz), 7.20 (d, 2H, J=8.4 Hz), 4.48 (s, 2H), 4.24 (m, 4H), 1.37 (m, 6H) ppm.

$^{13}C\{^1H\}$ NMR ($CDCl_3$, 120 MHz): δ 150.67, 150.63, 134.46, 130.51, 120.30, 120.27, 64.70, 64.65, 32.68, 16.11, 16.07 ppm.

MS (m/z): Calcd. for $[MH]^+$ 323.0, found 323.0.

Synthesis Example 3. Synthesis of Compound Represented by Chemical Formula 4

Generally known 6-methoxy-2,3-dihydro-1H-xanthene-4-carbaldehyde was prepared.

After dissolving the 6-methoxy-2,3-dihydro-1H-xanthene-4-carbaldehyde (200 mg, 0.82 mmol) in DCM (8.3 mL), a 1 M $BBr_3$ DCM solution (20 eq, 16.5 mL, 16.5 mmol) was added at 0° C. and the mixture was stirred at 25° C. for 16 hours. Then, the mixture was added to a $NaHCO_3$ solution at 0° C. and the aqueous layer was extracted with DCM/MeOH (10:1 mixture, 2×50 mL). Then, the organic layer was washed with $H_2O$ and dried with $Na_2SO_4$. Then, after removing the solvent, the product was dried in vacuo to finally obtain a compound represented by Chemical Formula 4 (6-hydroxy-2,3-dihydro-1H-xanthene-4-carbaldehyde) as yellow solid (184 mg, 97%).

The result of $^1H$ NMR spectroscopy and mass spectroscopy of the finally obtained compound is as follows.

$^1H$ NMR (DMSO-$d_6$, 600 MHz): δ 10.18 (s, 1H), 7.19 (d, 1H, J=9.0 Hz), 6.92 (s, 1H), 6.61 (sd, 1H, J=2.4 Hz), 6.59 (dd, 1H, J=8.4, 2.4 Hz), 2.53 (t, 2H, J=5.4 Hz), 2.27 (t, 2H, J=5.4 Hz), 1.60 (m, 2H) ppm.

MS (m/z): Calcd. for $[MH]^+$ 229.1, found 229.1.

Synthesis Example 4. Synthesis of Compound Represented by Chemical Formula 6

A mixture containing the compound represented by Chemical Formula 4 (278 mg, 1.22 mmol) and the compound represented by Chemical Formula 5 (512 mg, 1.58 mmol) and $Cs_2CO_3$ (1.19 g, 3.66 mmol) was dissolved in anhydrous DMF (6 mL) and stirred at 50° C. for 4 hours under argon atmosphere.

After removing the solvent by evaporating, the reaction mixture was purified by silica column chromatography using ethyl acetate/n-hexane (volume ratio: 1/2 to 2/1) as an eluent to finally obtain a compound represented by Chemical Formula 6 (diethyl (4-(((4-formyl-2,3-dihydro-1H-xanthen-6-yl)oxy) methyl)phenyl) phosphate). The result of $^1H$ NMR spectroscopy and mass spectroscopy of the compound is as follows.

$^1H$ NMR ($CDCl_3$, 600 MHz): δ 10.23 (s, 1H), 7.34 (d, 2H, J=9.0 Hz), 7.18 (d, 2H, J=7.8 Hz), 7.02 (d, 1H, J=8.4 Hz), 6.65-6.63 (m, 2H), 6.58 (s, 1H), 4.98 (s, 2H), 4.18 (m, 4H), 2.50 (t, 2H, J=6.0 Hz), 2.38 (t, 2H, J=6.0 Hz), 1.66 (m, 2H), 1.30-1.27 (m, 6H) ppm.

MS (m/z): Calcd. for $[MH]^+$ 471.2, found 471.2.

Synthesis Example 5. Synthesis of Compound Represented by Chemical Formula 8

A mixture containing the compound represented by Chemical Formula 6 (159 mg, 0.32 mmol) prepared above and 1-ethyl-2,3,3-trimethyl-3H-indol-1-ium-5-sulfonate (114 mg, 0.42 mmol) was stirred at 40° C. for 20 hours under argon atmosphere. EtOAc (20 mL) was added to the blue reaction mixture. The resulting blue precipitate recovered by filtering and washed with EtOAc and ether to obtain a compound represented by Chemical Formula 8 ((E)-2-(2-(6-((4-(((diethoxyphosphoryl)oxy)benzyl)oxy)-2,3-dihydro-1H-xanthen-4-yl)vinyl)-1-ethyl-3,3-dimethyl-3H-indol-1-ium-5-sulfonate) as blue solid (208 mg, 90%). The result of $^1H$ NMR spectroscopy and mass spectroscopy of the compound is as follows.

$^1H$ NMR (DMSO-$d_6$, 400 MHz): δ 8.60 (d, 1H, J=14.8 Hz), 7.90 (s, 1H), 7.77 (d, 1H, J=7.6 Hz), 7.63 (d, 1H, J=8.4 Hz), 7.58-7.55 (m, 3H), 7.51 (s, 1H), 7.28 (d, 2H, J=8.4 Hz), 7.21 (sd, 1H, J=1.6 Hz), 7.09 (dd, 1H, J=8.8, 2.4 Hz), 6.57 (d, 1H, J=14.8 Hz), 5.28 (s, 2H), 4.45 (q, 2H, J=7.2 Hz), 4.19 (m, 4H), 2.73-2.67 (m, 4H), 1.84-1.81 (m, 2H), 1.76 (s, 6H), 1.38 (t, 3H, J=7.2 Hz), 1.27 (t, 6H, J=7.2 Hz) ppm.

MS (m/z): Calcd. for [MH]$^+$ 720.2, found 720.2.

Synthesis Example 6. Synthesis of Compound Represented by Chemical Formula 10

A mixture containing the compound represented by Chemical Formula 4 (220 mg, 0.96 mmol) prepared above and Cs$_2$CO$_3$ (941 mg, 2.88 mmol) was dissolved in anhydrous DMF (5 mL) and diethyl chlorophosphate (0.17 mL, 1.15 mmol) was added. The reaction mixture was stirred at room temperature for 4 hours under argon atmosphere. The mixture was diluted with EtOAc (30 mL), extracted with H$_2$O (30 mL) and washed with brine (30 mL). The organic layer was dried with Na$_2$SO$_4$ and concentrated under reduced pressure. The obtained product was purified by silica column chromatography using ethyl acetate/n-hexane (volume ratio: 1/2 to 1/1) as an eluent to obtain a compound represented by Chemical Formula 10 ((4-formyl-2,3-dihydro-1H-xanthen-6-yl)phosphate, 327 mg, 93%) as yellow solid. The result of $^1$H NMR spectroscopy and mass spectroscopy of the compound is as follows.

$^1$H NMR (CDCl$_3$, 400 MHz): δ 10.31 (s, 1H), 7.14 (d, 1H, J=8.4 Hz), 7.01 (s, 1H), 6.98 (m, 1H), 6.65 (s, 1H), 4.28-4.20 (m, 4H), 2.59 (t, 2H, J=6.0 Hz), 2.45 (t, 2H, J=6.0 Hz), 1.75 (m, 2H), 1.40 (m, 6H) ppm.

MS (m/z): Calcd. for [MH]$^+$ 365.1, found 365.1.

Synthesis Example 7. Synthesis of Compound Represented by Chemical Formula 11

A mixture containing the compound represented by Chemical Formula 10 (135 mg, 0.37 mmol) prepared above and 1-ethyl-2,3,3-triethyl-3H-indol-1-ium-5-sulfonate (128 mg, 0.48 mmol) was dissolved in anhydrous Ac$_2$O (7.4 mL) and stirred at 40° C. for 20 hours under argon atmosphere. After adding EtOAc (20 mL) to the obtained blue reaction mixture, the resulting precipitate was recovered by filtering. The filtrate was washed with ether to obtain a compound represented by Chemical Formula 11 ((E)-2-(2-(6-((diethoxyphosphoryl)oxy)-2,3-dihydro-1H-xanthen-4-yl)vinyl)-1-ethyl-3,3-dimethyl-3H-indol-1-ium-5-sulfonate, 110 mg, 48%) as blue solid. The result of $^1$H NMR spectroscopy and mass spectroscopy of the compound is as follows.

$^1$H NMR (CDCl$_3$, 400 MHz): δ 8.60 (d, 1H, J=14.8 Hz), 7.95 (s, 1H), 7.79 (d, 1H, J=8.0 Hz), 7.71 (d, 1H, J=8.0 Hz), 7.61 (d, 1H, J=8.4 Hz), 7.42 (s, 1H), 7.40 (s, 1H), 7.22 (dd, 1H, J=8.4, 1.2 Hz), 6.68 (d, 1H, J=15.2 Hz), 4.51 (q, 2H, J=6.8 Hz), 4.26 (m, 4H), 2.72 (m, 4H), 1.84 (m, 2H), 1.77 (s, 6H), 1.40 (t, 3H, J=7.2 Hz), 1.33 (t, 6H, J=7.2 Hz) ppm.

MS (m/z): Calcd. for [MH]$^+$ 614.2, found 614.2.

Synthesis Example 8. Synthesis of Compound Represented by Chemical Formula 2

Figure 2A:
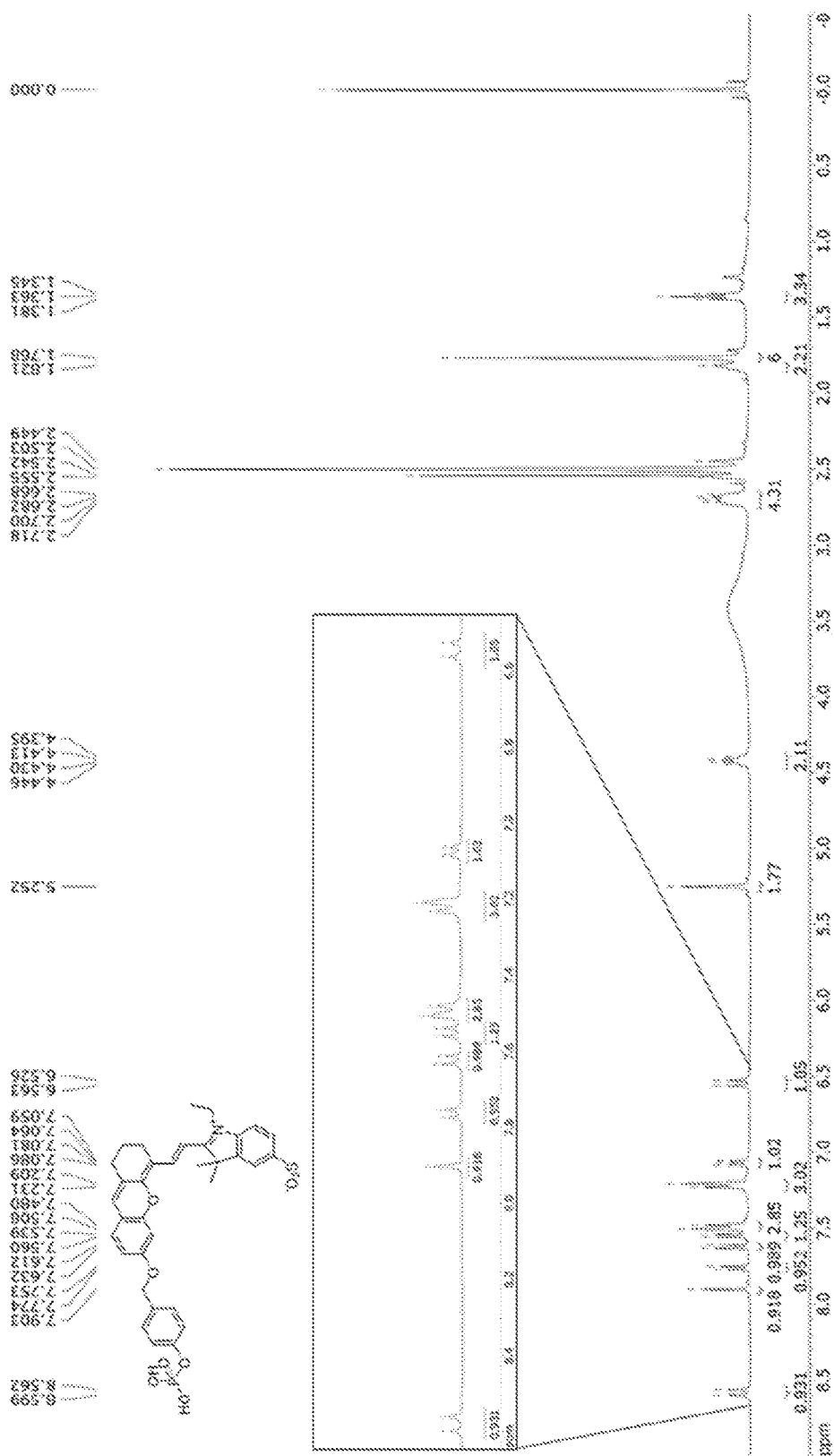
FIGS. 2A and 2B show the NMR spectrum of a compound prepared in Synthesis Example 8.
Figure 2B:
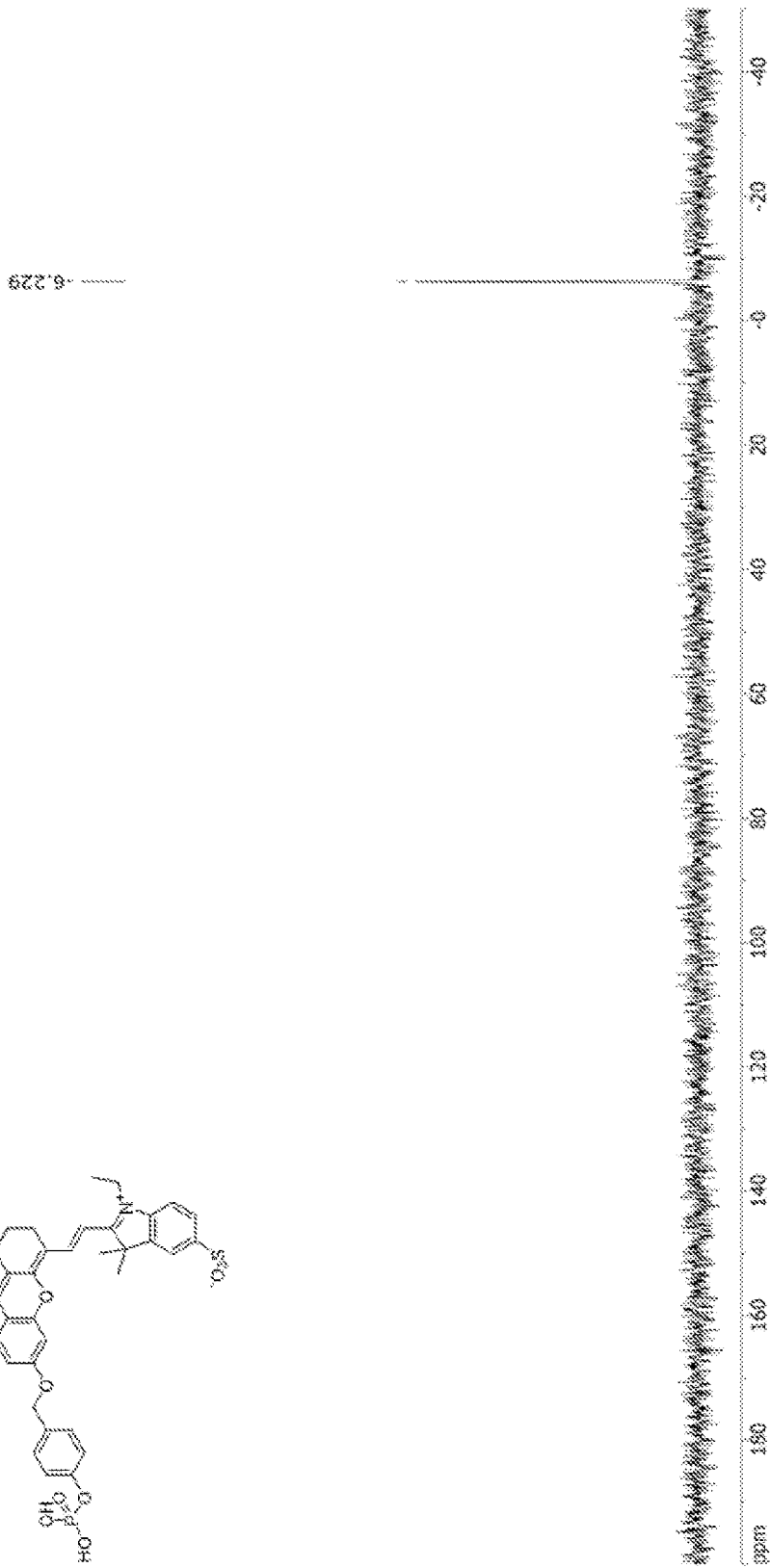

The compound represented by Chemical Formula 8 (192 mg, 0.27 mmol) prepared above was dissolved in anhydrous DCM (50 mL) and iodotrimethylsilane (0.38 mL, 2.67 mmol) was added at 0° C. Then, the mixture was stirred at room temperature for 3 hours under argon atmosphere. After removing the solvent, MeOH (50 mL) was added and the reaction mixture was stirred for 2 hours. After removing the solvent, the mixture was purified by reverse-phase HPLC to obtain a compound represented by Chemical Formula 2 ((E)-1-ethyl-3,3-dimethyl-2-(2-(6-((4-(phosphonooxy)benzyl)oxy)-2,3-dihydro-1H-xanthen-4-yl)vinyl)-3H-indol-1-ium-5-sulfonate, 45 mg, 26%). The result of $^1$H NMR and $^{31}$P{$^1$H} NMR spectroscopy and mass spectroscopy of the compound is as follows (see FIGS. 2A and 2B).

The 'compound represented by Chemical Formula 2' was named as 'NIR-Phos-1'.

[Chemical Formula 2]

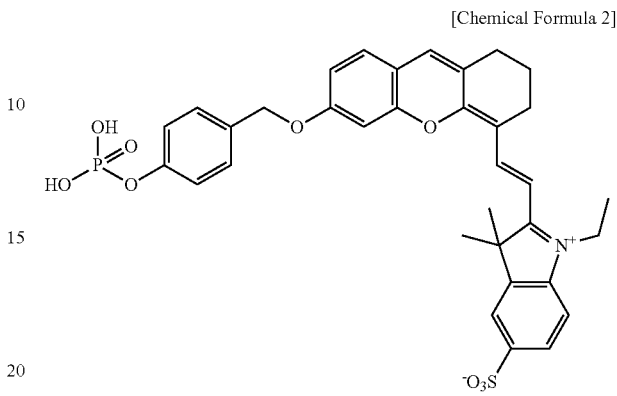

$^1$H NMR (DMSO-d$_6$, 400 MHz): δ 8.60 (d, 1H, J=14.8 Hz), 7.90 (s, 1H), 7.77 (d, 1H, J=8.4 Hz), 7.63 (d, 1H, J=8.0 Hz), 7.56 (d, 1H, J=8.8 Hz), 7.51-7.48 (m, 3H), 7.23-7.21 (m, 3H), 7.08 (dd, 1H, J=8.4, 2.0 Hz), 6.56 (d, 1H, J=14.8 Hz), 5.25 (s, 2H), 4.43 (q, 2H, J=7.6 Hz), 2.72-2.67 (m, 4H), 1.82 (m, 2H), 1.76 (s, 6H), 1.38 (t, 3H, J=7.2 Hz) ppm.

$^{31}$P{$^1$H} NMR (DMSO-d$_6$, 400 MHz): δ-6.22 ppm.

MS (m/z): Calcd. for [MH]$^+$ 664.2, found 664.2.

Synthesis Example 9. Synthesis of Compound Represented by Chemical Formula 3

Figure 3A:
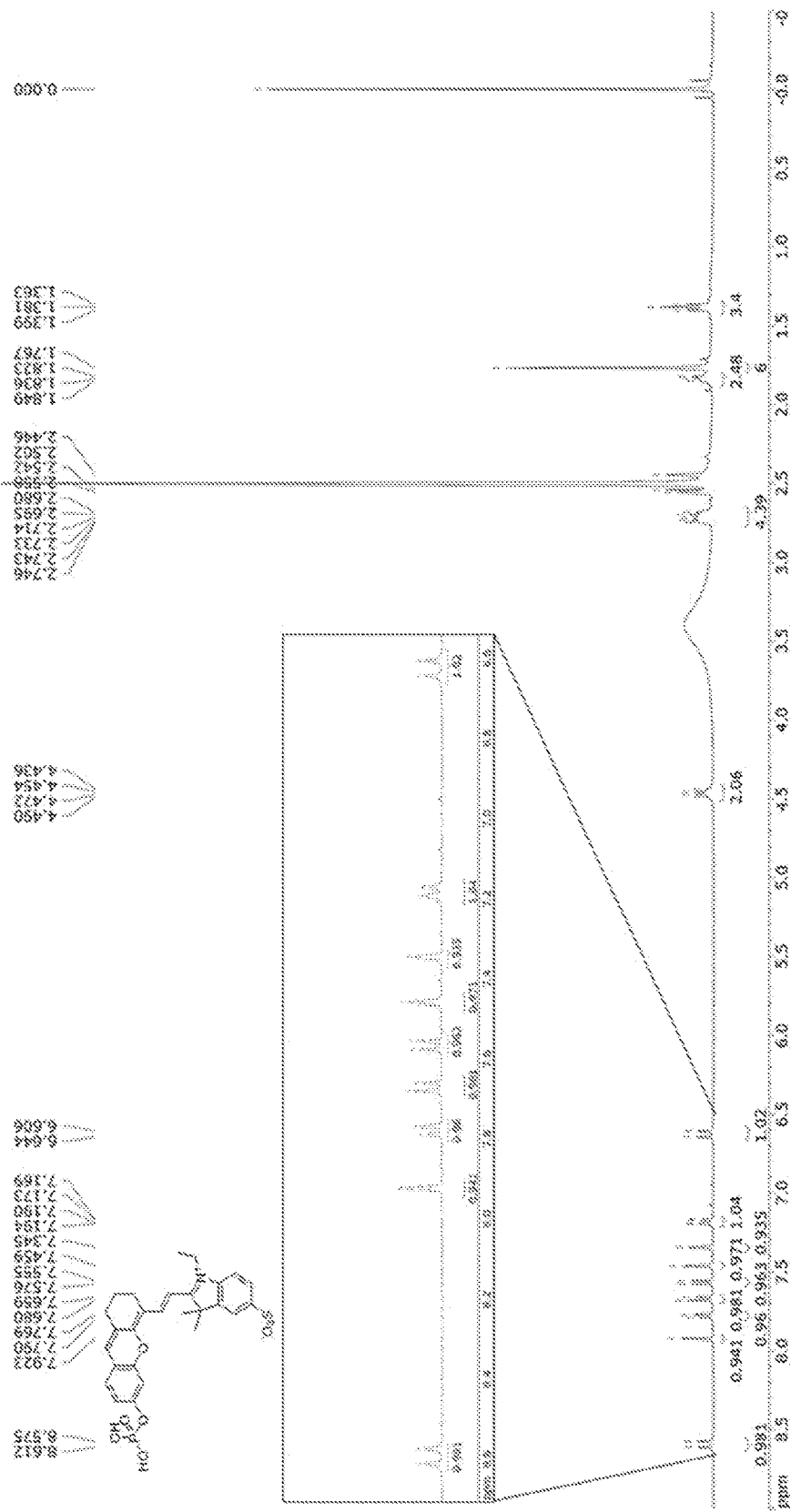
FIGS. 3A and 3B show the NMR spectrum of a compound prepared in Synthesis Example 9.
Figure 3B:
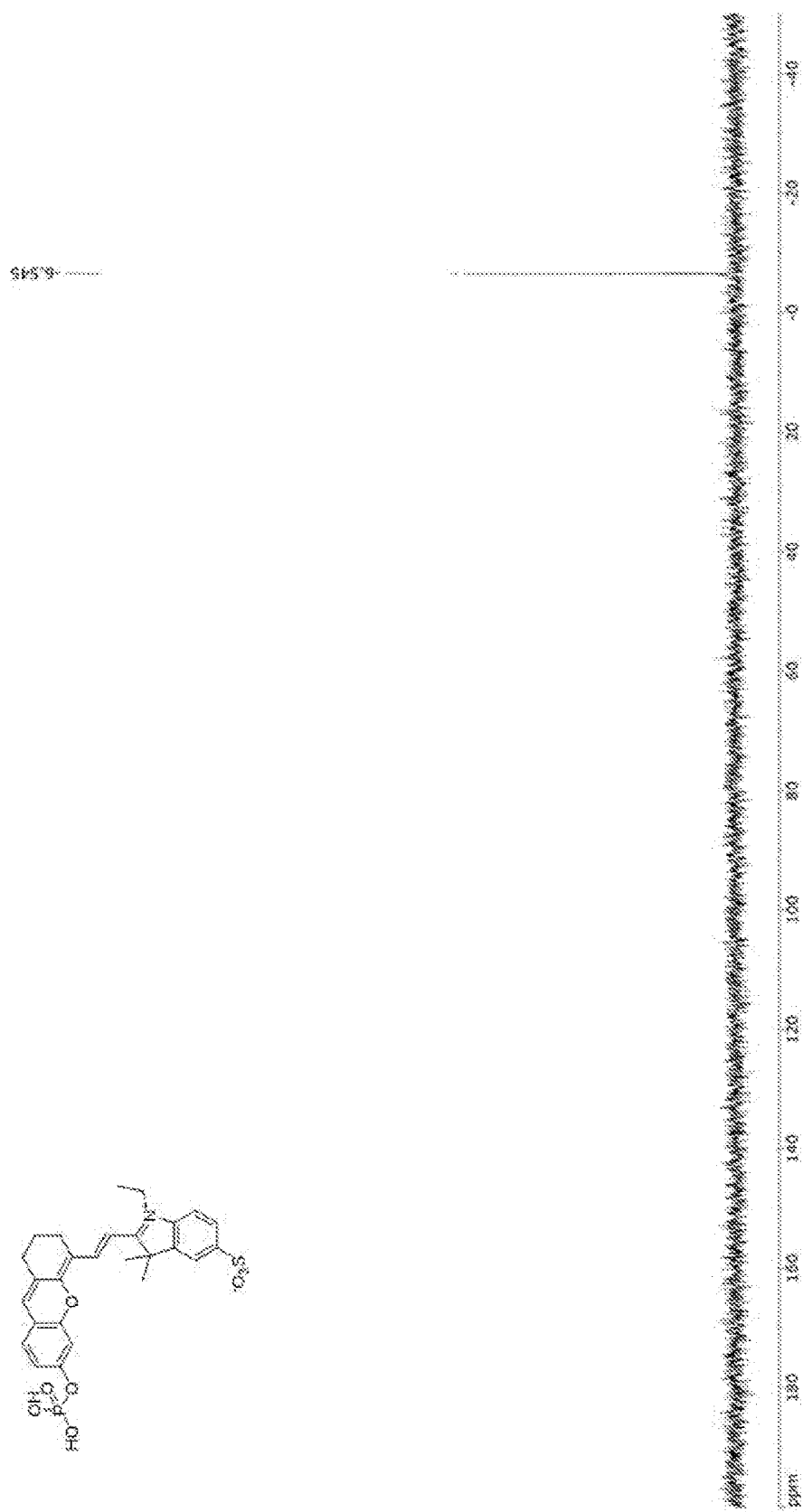

The compound represented by Chemical Formula 11 (110 mg, 0.18 mmol) prepared above was dissolved in anhydrous DCM (18 mL) and iodotrimethylsilane (0.25 mL, 1.79 mmol) was added at 0° C. Then, the mixture was stirred at room temperature for 3 hours under argon atmosphere. After removing the solvent and adding MeOH (18 mL), the reaction mixture was stirred for 2 hours. Then, after removing the solvent, the mixture was purified by reverse-phase HPLC to obtain a compound represented by Chemical Formula 3 ((E)-1-ethyl-3,3-dimethyl-2-(2-(6-(phosphonooxy)-2,3-dihydro-1H-xanthen-4-yl)vinyl)-3H-indol-1-ium-5-sulfonate, 30 mg, 30%). The result of $^1$H NMR and $^{31}$P{$^1$H} NMR spectroscopy and mass spectroscopy of the compound is as follows (see FIGS. 3A and 3B).

The 'compound represented by Chemical Formula 3' was named as 'NIR-Phos-2'.

[Chemical Formula 3]

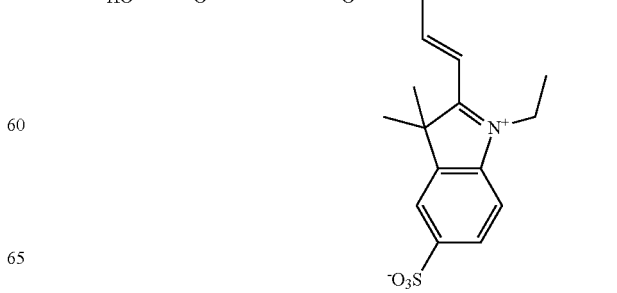

¹H NMR (DMSO-d$_6$, 400 MHz): δ 8.61 (d, 1H, J=15.6 Hz), 7.92 (sd, 1H, J=1.2 Hz), 7.79 (dd, 1H, J=8.4, 1.2 Hz), 7.68 (d, 1H, J=8.8 Hz), 7.57 (d, 1H, J=8.0 Hz), 7.46 (s, 1H), 7.35 (s, 1H), 7.19 (dd, 1H, J=8.8, 2.4 Hz), 6.64 (d, 1H, J=15.2 Hz), 4.49 (q, 2H, J=7.6 Hz), 2.74-2.68 (m, 4H), 1.85 (m, 2H), 1.76 (s, 6H), 1.39 (t, 3H, J=7.2 Hz) ppm.

$^{31}$P{¹H} NMR (DMSO-d$_6$, 400 MHz): δ-6.54 ppm.

MS (m/z): Calcd. For [MH]$^+$ 558.1, found 558.1.

Example 1. Evaluation of Reactivity of ALP

Example 1-1. Evaluation of Sensitivity for ALP

The reaction of ALP was evaluated for the NIR-Phos-1 and NIR-Phos-2 fluorescent probes.

After pre-treating with the ALP inhibitor p-BTO (p-bromotetramisole oxalate) at 1-2.5 mM, the fluorescent probe was mixed with ALP. The result is shown in FIGS. 4A and 4B.

Figure 4A:
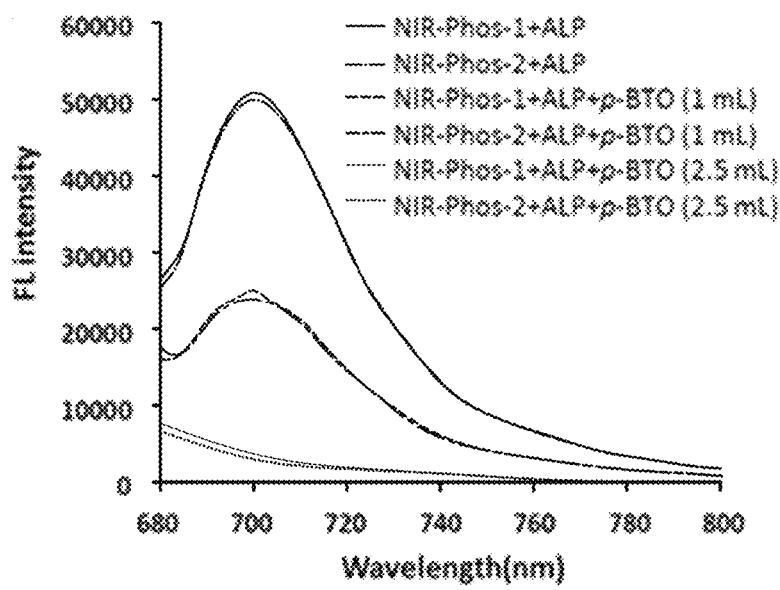
FIGS. 4A and 4B show the fluorescence sensitivity of a fluorescent probe.
Figure 4B:
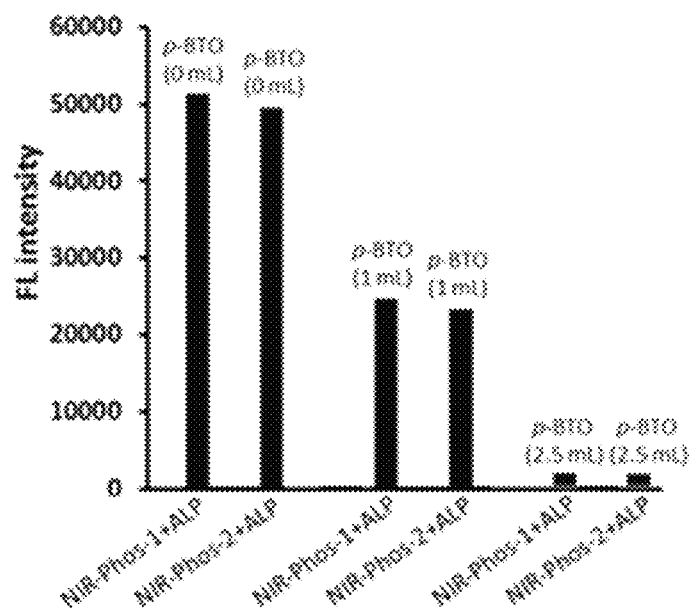

Referring to FIGS. 4A and 4B, the fluorescent probe pre-treated with p-BTO showed distinct decrease in fluorescence intensity as compared to the solution not containing p-BTO. In addition, it was confirmed that the hydrolysis of the fluorescent probe and ALP is inhibited by p-BTO because the fluorescence intensity of the mixture of the fluorescent probe and ALP decreased gradually as the concentration of p-BTO was increased.

Accordingly, it can be seen that the NIR-Phos-1 and NIR-Phos-2 fluorescent probes have good sensitivity for ALP.

Example 1-2. Evaluation of Fluorescence Response Depending on ALP Concentration

Reactivity depending on ALP concentration was evaluated for the NIR-Phos-1 and NIR-Phos-2 fluorescent probes. After dissolving the fluorescent probe (5 μM) in a Tri-HCl buffer (10 mM, pH 7.4), the fluorescence spectrum occurring as a result of reaction with ALP (0.1 UmL$^{-1}$) was investigated. The result is shown in FIGS. 5A to 5D.

Figure 5A:
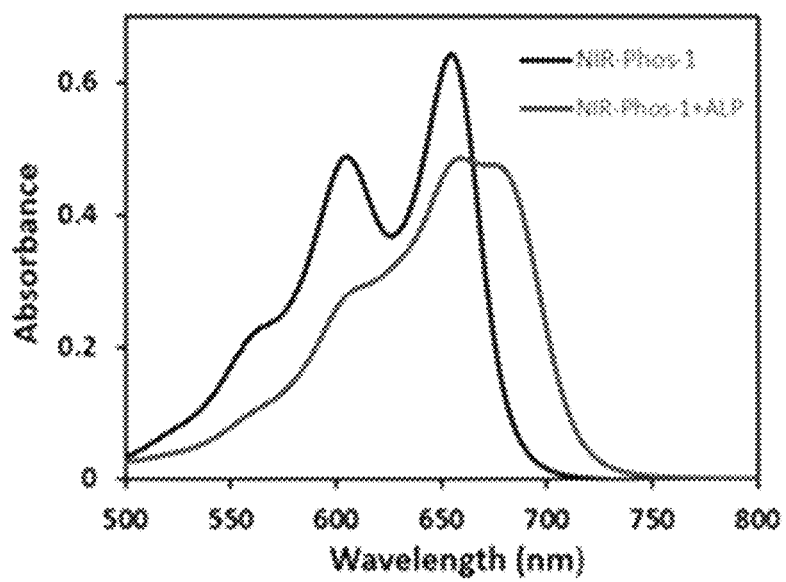
FIGS. 5A to 5D show the reactivity of a fluorescent probe depending on concentration.
Figure 5B:
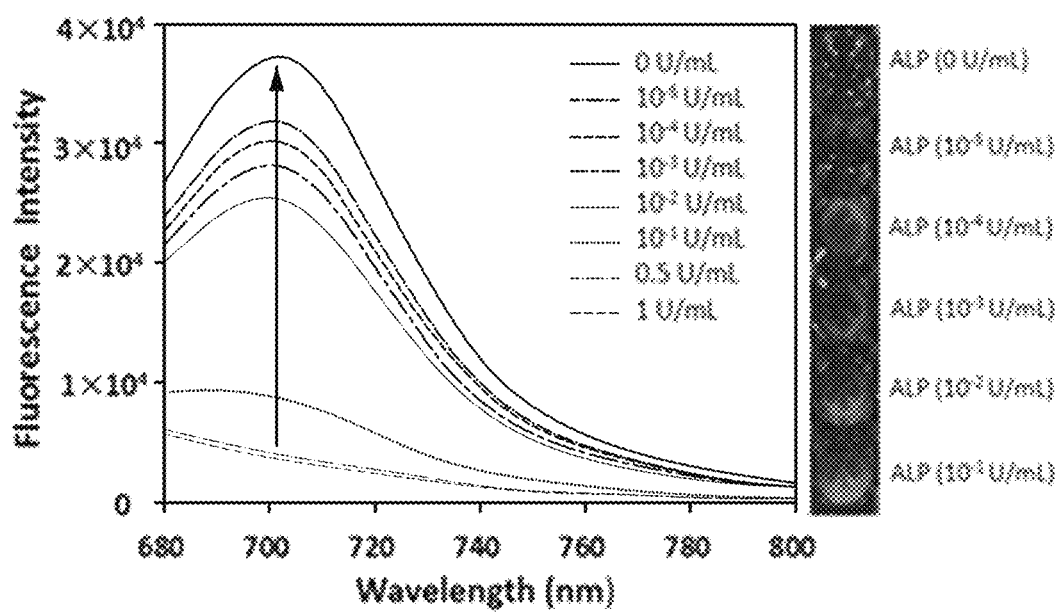
Figure 5C:
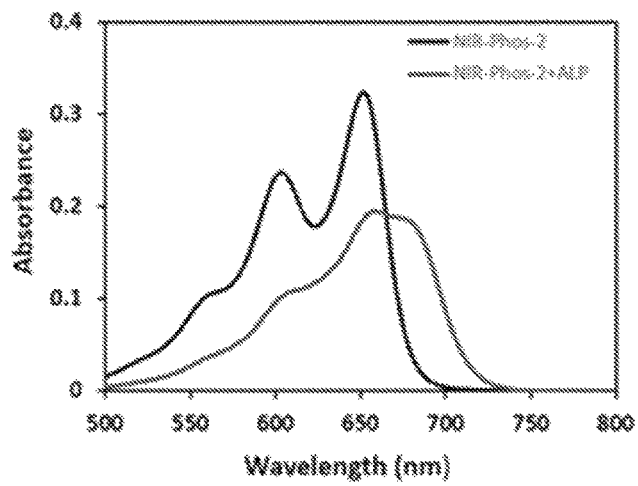

Referring to FIG. 5A and FIG. 5C, the NIR-Phos-1 and NIR-Phos-2 fluorescent probes exhibited UV absorption bands at 600-700 nm and a new absorption peak was observed at 710 nm in the presence of ALP.

Accordingly, it can be seen that the NIR-Phos-1 and NIR-Phos-2 fluorescent probes exhibit fluorescence at 710 nm ($\lambda_{ex}$=685 nm) due to dephosphorylation of ALP, which allows for fast and accurate detection of ALP.

In addition, it was confirmed that the fluorescent probe treated with ALP exhibits high quantum yields ($\phi_f$=0.65 and 0.64) in an aqueous medium when excited at $\lambda_{max}$ (685 nm).

Figure 5D:
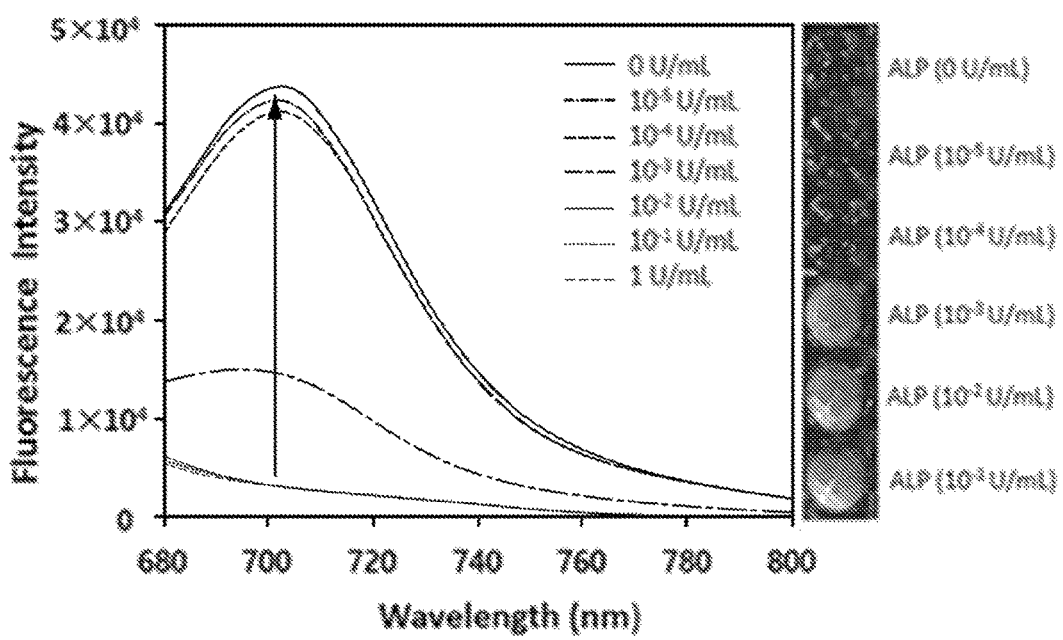
Figure 6A:
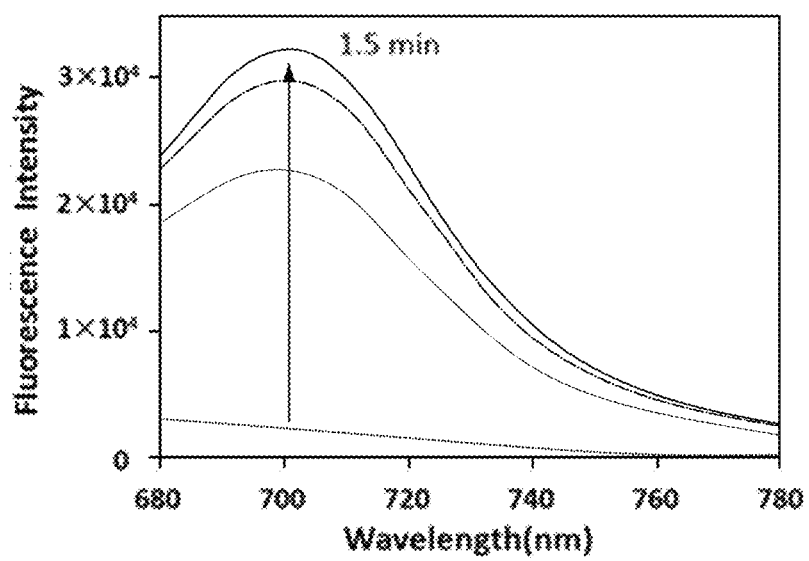
FIGS. 6A to 6D show the reactivity of a fluorescent probe depending on time.
Figure 6B:
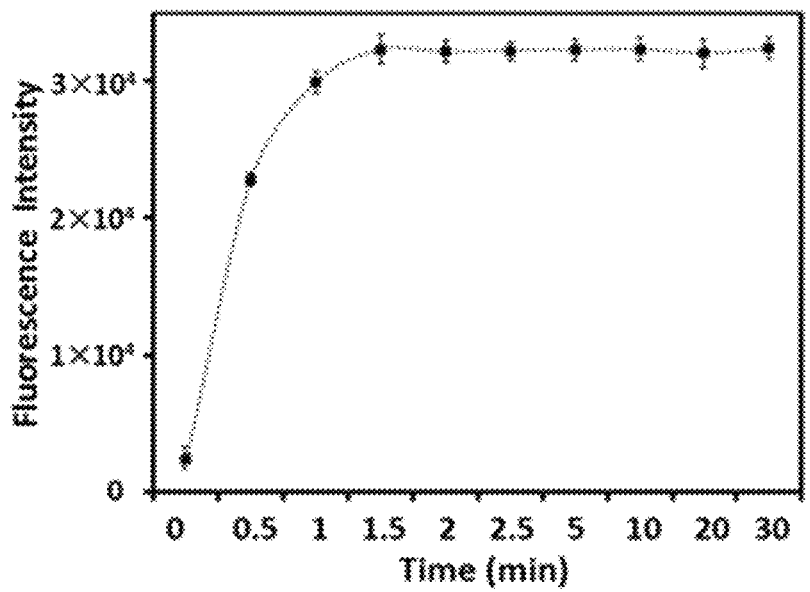
Figure 6C:
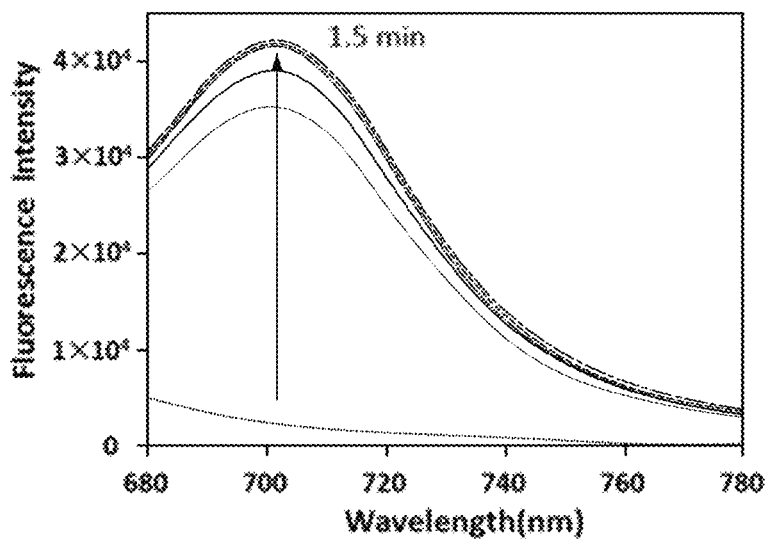
Figure 6D:
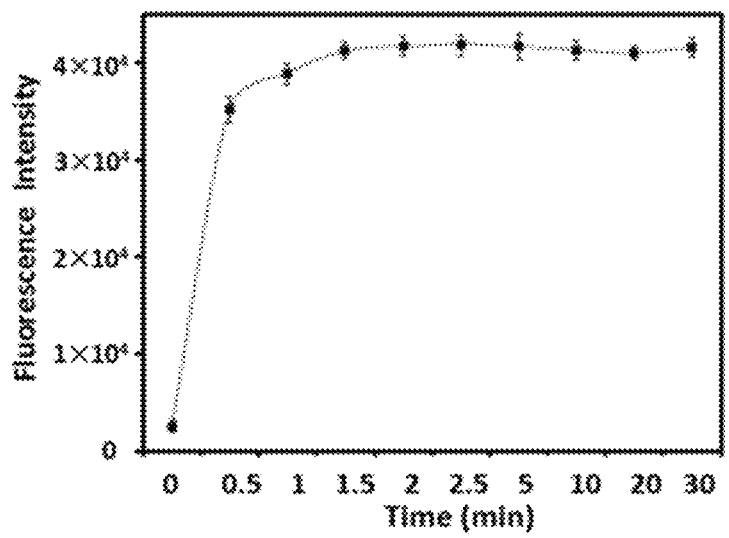

From FIG. 5B and FIG. 5D, it can be seen that fluorescence spectra are changed variously by adding a Tris-HCl buffer (10 mM, pH 7.4) to ALP (10$^{-5}$ to 1.0 UmL$^{-1}$) of various concentrations.

It can be seen that the NIR-Phos-1 and NIR-Phos-2 fluorescent probes can detect ALP even at very low concentrations and the fluorescence intensity is increased remarkably with the concentration. Also, it was revealed that the reaction proceeds quickly with high sensitivity because ALP was detected within 2 minutes. In addition, it was confirmed that 0.02-0.14 UmL$^{-1}$ of ALP, corresponding to blood level in healthy adults, can be detected by the NIR-Phos-1 and NIR-Phos-2 fluorescent probes with high sensitivity.

Example 1-3. Evaluation of Fluorescence Response Depending on Time

Reactivity depending on time was evaluated for the NIR-Phos-1 and NIR-Phos-2 fluorescent probes. The result is shown in FIGS. 6A to 6D.

Referring to FIGS. 6A to 6D, it was confirmed that fluorescence increased rapidly within 30 seconds after the addition of ALP and the maximum fluorescence intensity was achieved in 1.5 minutes. That is to say, it can be seen that the fluorescent probe may be used for real-time monitoring of ALP because it responds very quickly to ALP.

Example 1-4. Evaluation of Reactivity Depending on pH

In order to investigate the effect of pH for the NIR-Phos-1 and NIR-Phos-2 fluorescent probes, fluorescence spectra were measured for solutions of various pH (pH 1 to 12). The pH dependence of the fluorescent probe was determined based on the fluorescence intensity at 710 nm ($\lambda_{ex}$=675 nm). The result is shown in FIGS. 7A and 7B.

Figure 7A:
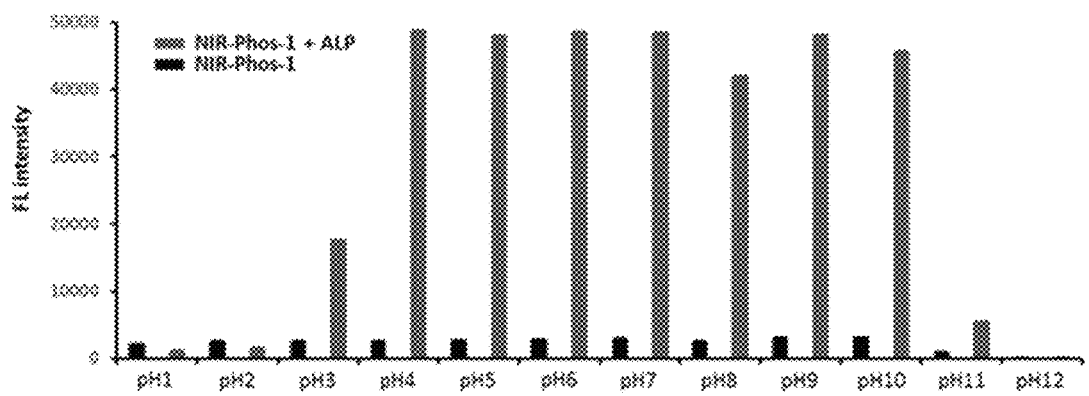
FIGS. 7A and 7B show the reactivity of a fluorescent probe depending on pH.
Figure 7B:
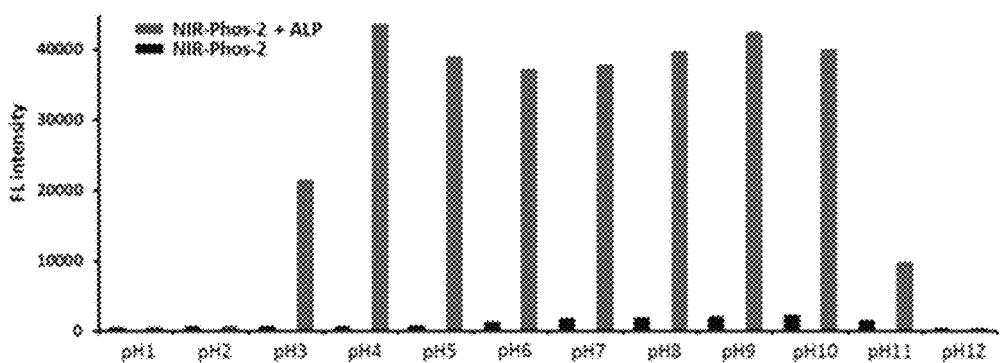
Figure 8A:
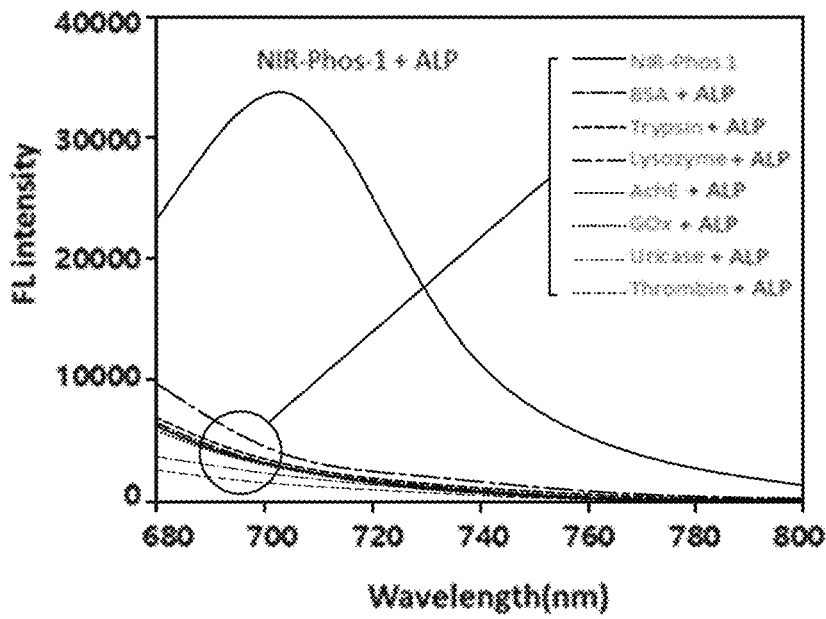
FIGS. 8A to 8D show selective detection of ALP by a fluorescent probe.
Figure 8B:
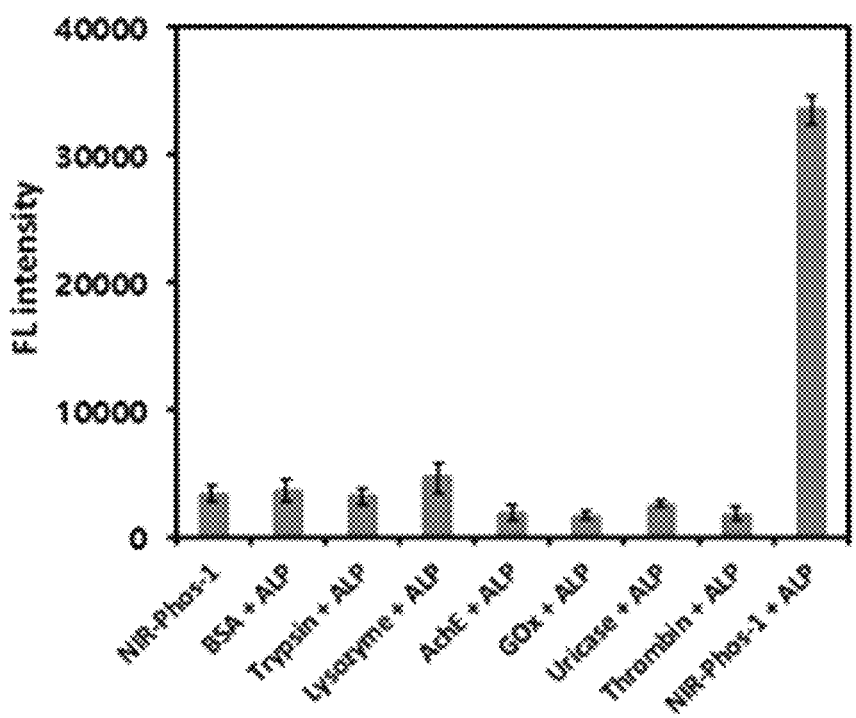
Figure 8C:
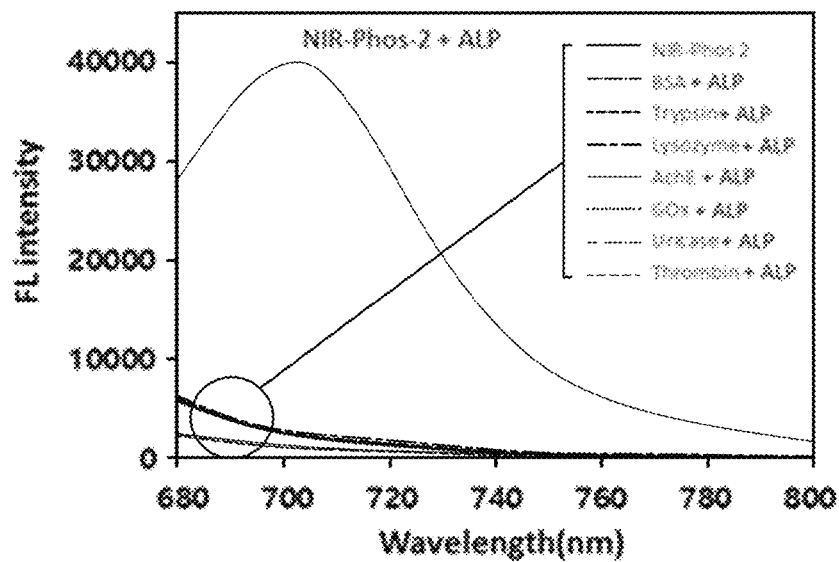
Figure 8D:
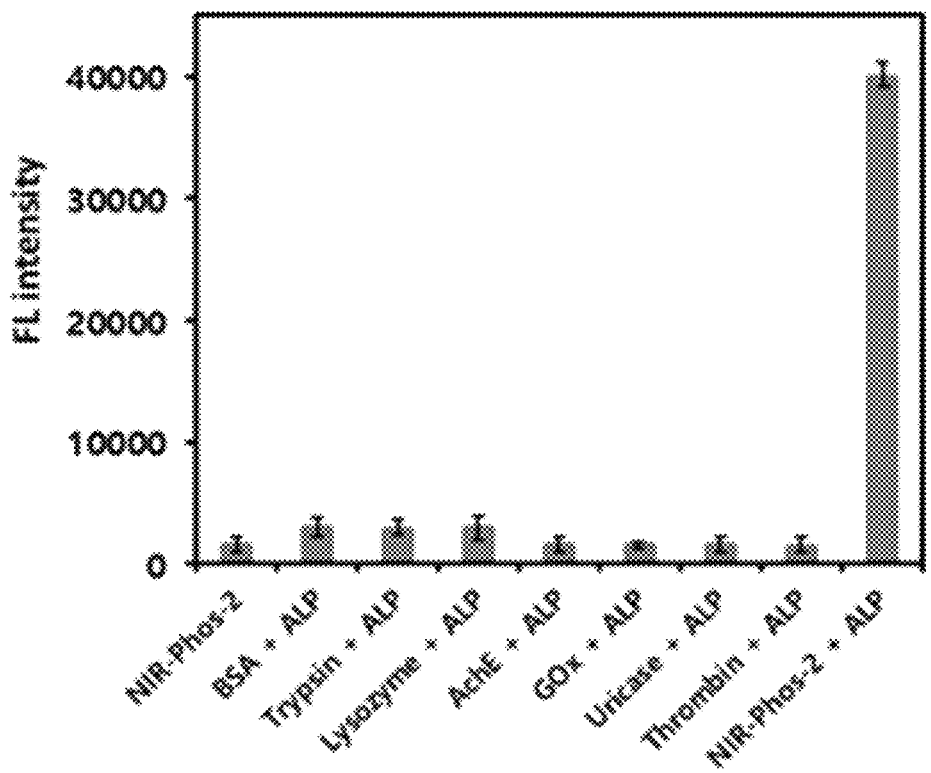

Referring to FIGS. 7A and 7B, although no distinct response was observed under highly acidic or basic conditions (pH<3 and pH>10), fluorescence response was observed under other pH conditions.

Accordingly, it can be seen that stable detection is possible with the fluorescent probe of the present disclosure under physiological conditions of pH 3 to 10.

Example 2. Evaluation of Selective ALP Detection

It was investigate whether the NIR-Phos-1 and NIR-Phos-2 fluorescent probes can selectively detect ALP.

ALP, BSA, trypsin, lysozyme, acetylcholinesterase (AcHE), glucose oxidase (GOx), uricase and thrombin were used for the evaluation. The result is shown in FIGS. 8A to 8D.

Referring to FIGS. 8A to 8D, the NIR-Phos-1 and NIR-Phos-2 fluorescent probes exhibited the highest fluorescence intensity when ALP was added. Accordingly, it can be seen that the NIR-Phos-1 and NIR-Phos-2 fluorescent probes can selectively detect ALP only.

Example 3. Fluorescence Stability Test

The photostability of a fluorescent probe is important for in-vitro and in-vivo fluorescence detection. Therefore, the photostability of the NIR-Phos-1 and NIR-Phos-2 fluorescent probes was evaluated by irradiating light at 685 nm from a 150-W xenon lamp for 1 hour in a Tris-HCl buffer (10 mM, pH 7.4) and measuring the change in fluorescence intensity. The result is shown in FIGS. 9A and 9B.

Figure 9A:
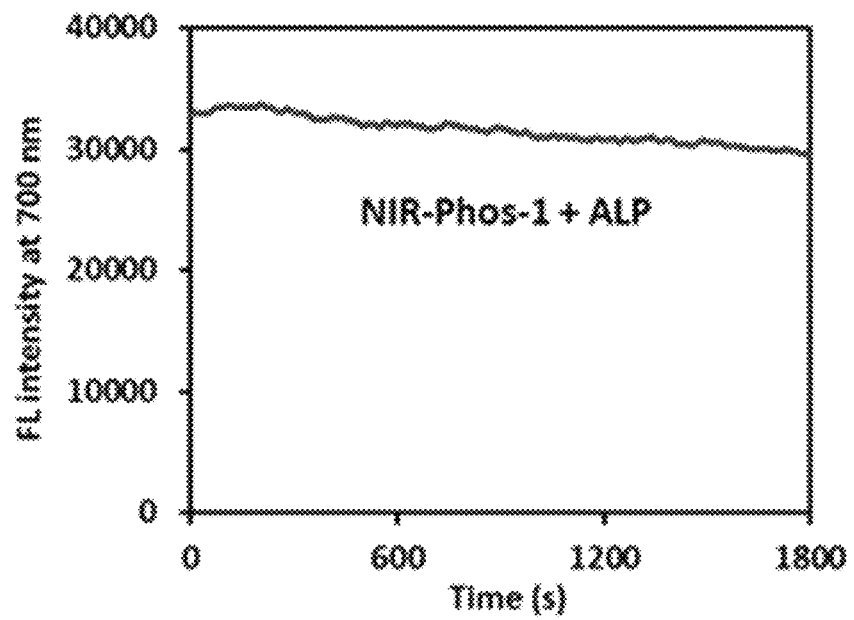
FIGS. 9A and 9B show the fluorescence stability of a fluorescent probe.
Figure 9B:
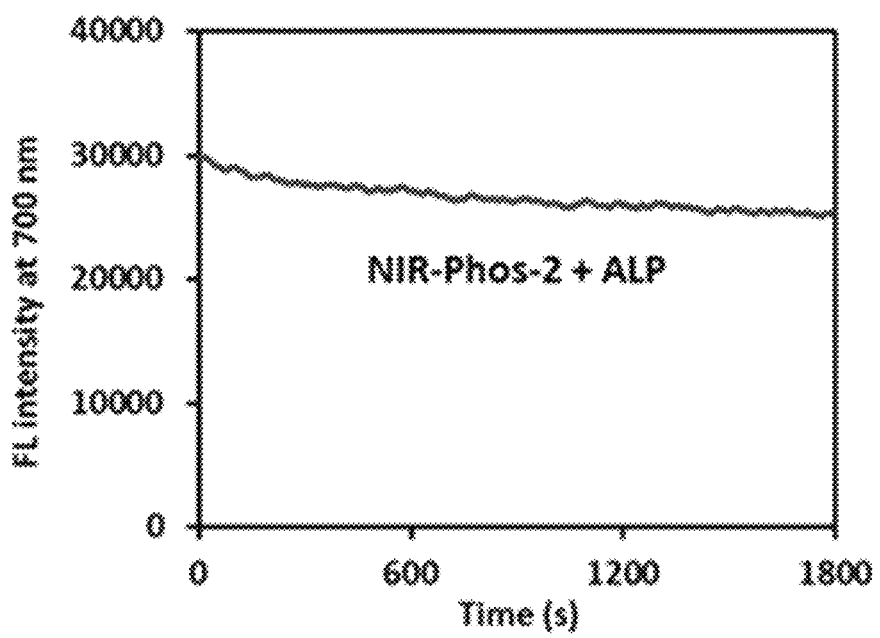
Figure 10A:
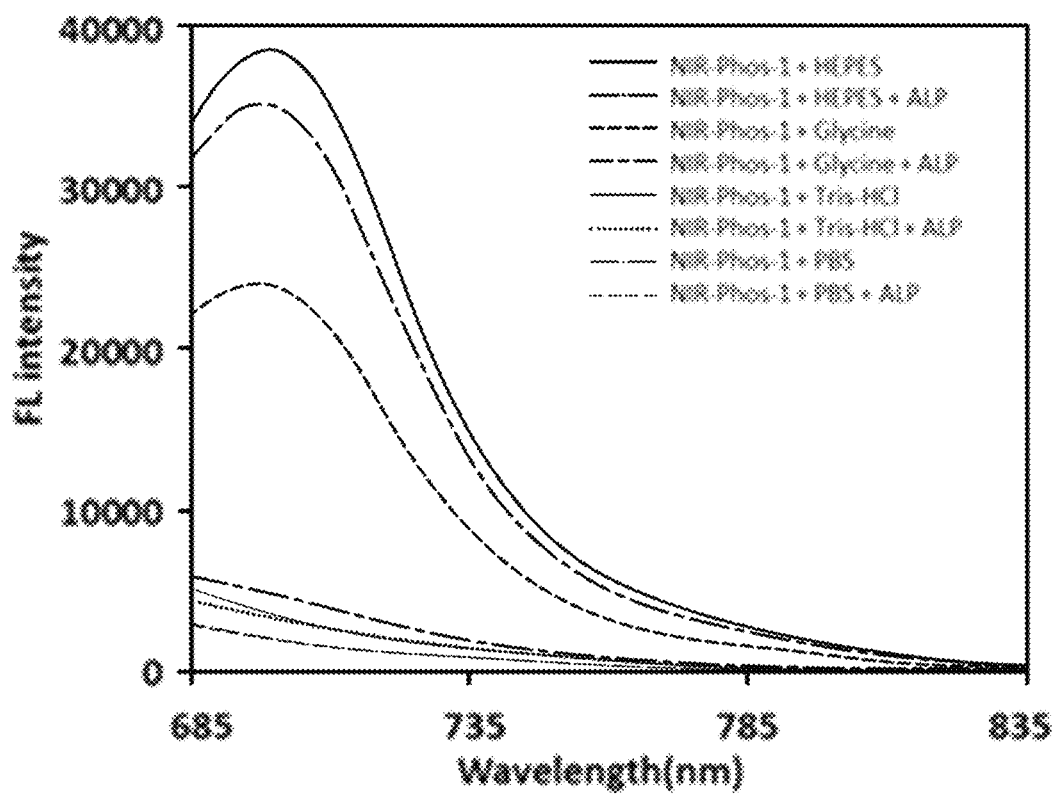
FIGS. 10A to 10D show the fluorescence spectrum of a fluorescent probe depending on buffer solutions.
Figure 10B:
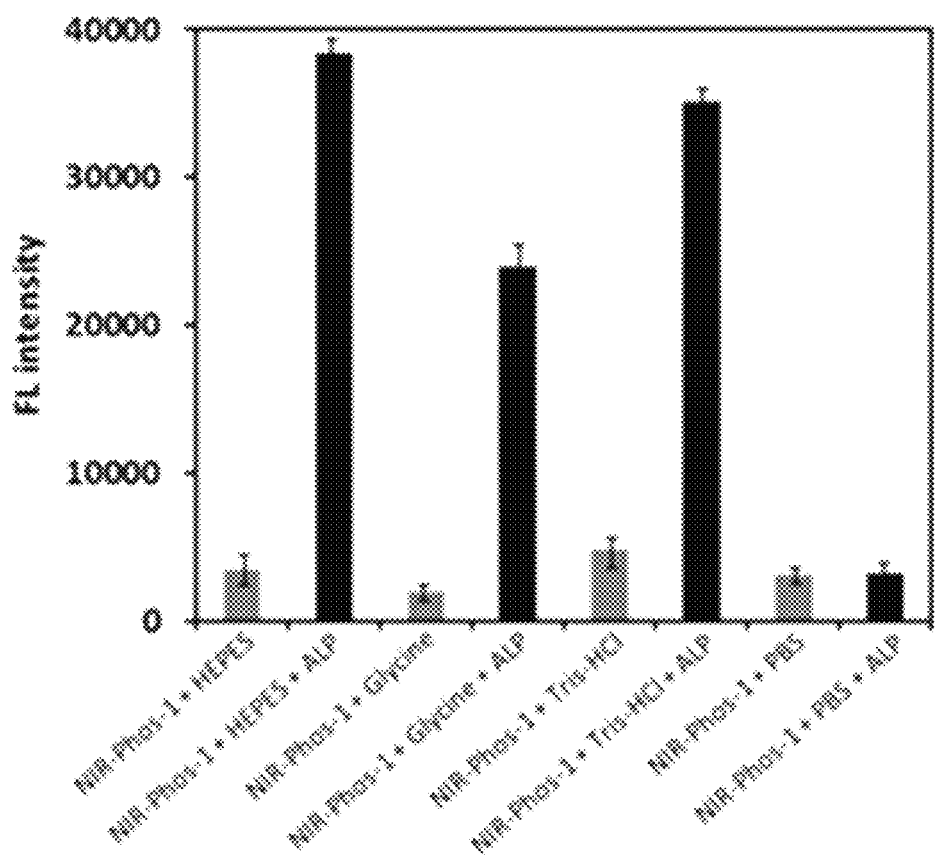
Figure 10C:
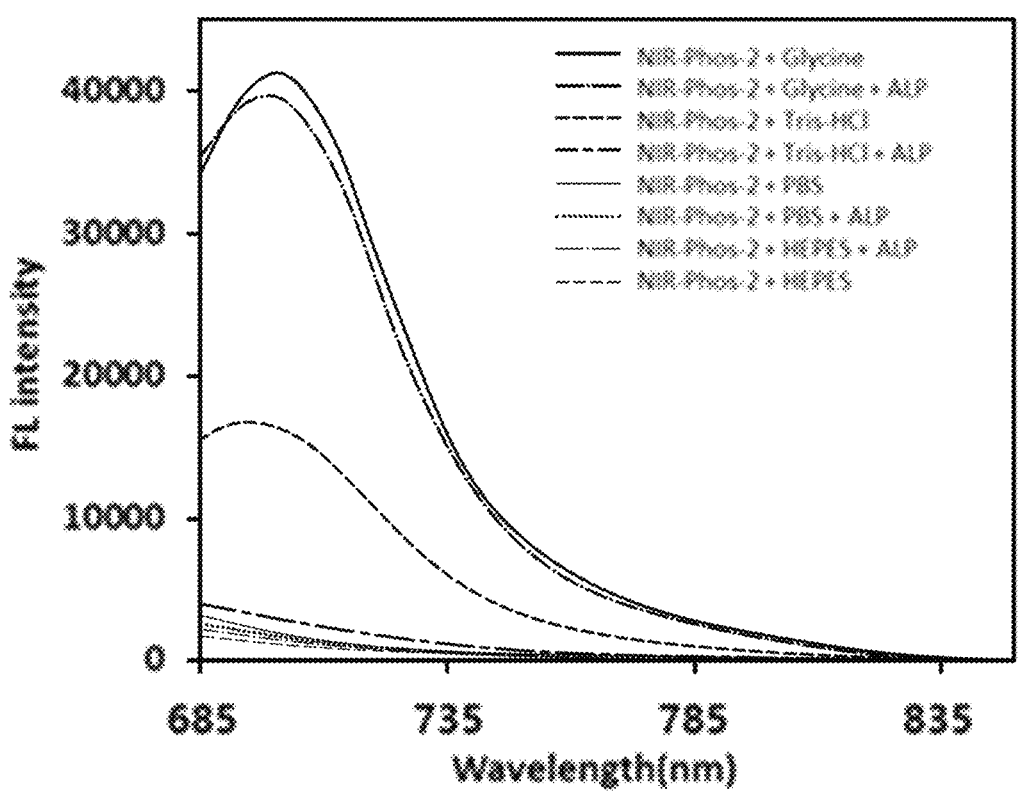
Figure 10D:
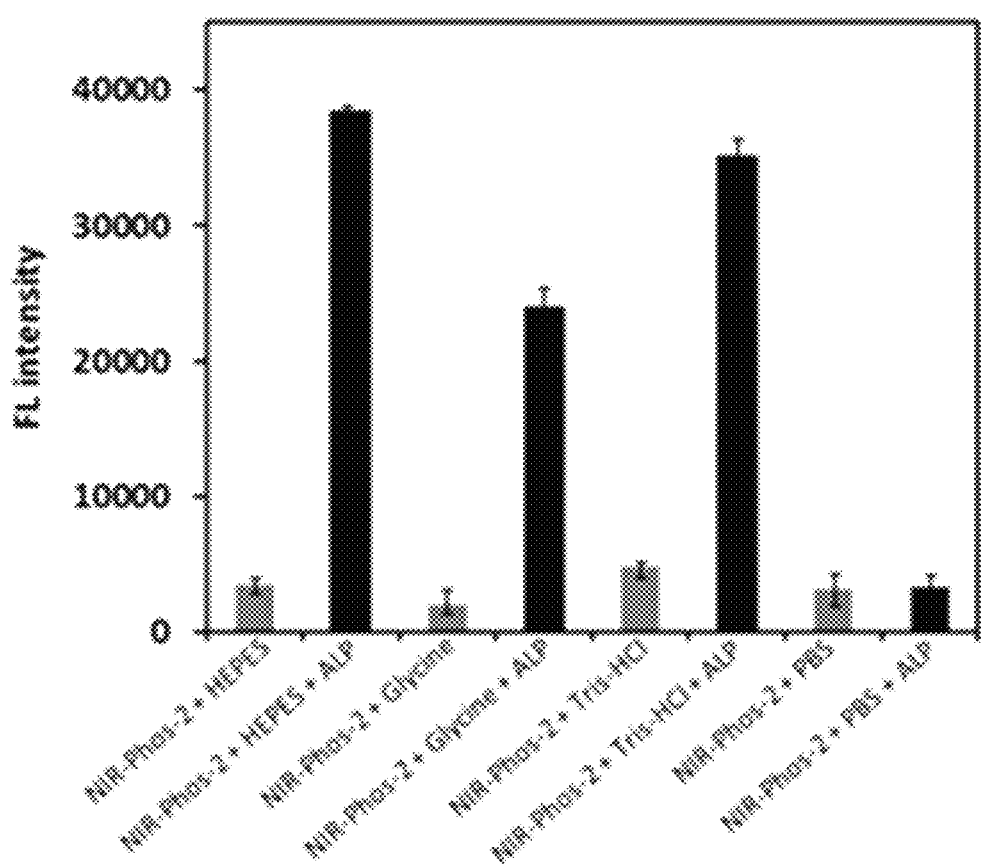

Referring to FIGS. 9A and 9B, it can be seen that the NIR-Phos-1 and NIR-Phos-2 fluorescent probes have superior photostability because the decrease in fluorescence intensity with time is insignificant.

Example 4. Measurement of Fluorescence Spectrum Depending on Buffer Solutions

The fluorescence spectra of the NIR-Phos-1 and NIR-Phos-2 fluorescent probes (5 μM) with ALP (0.1 UmL$^{-1}$) were measured using various buffer solutions. The result is shown in FIGS. 10A to 10D. As the buffer solutions, Tris-HCl (10 mM, pH 7.4), HEPES (10 mM, pH 7.4), glycine (10 mM, pH 7.4) and PBS (10 mM, pH 7.4) were used.

Referring to FIGS. 10A to 10D, it can be seen that the phosphate in the PBS buffer is the most likely to interfere with the reaction between ALP and the fluorescent probe because the change in fluorescence intensity was not observed in the PBS buffer.

Example 5. Evaluation of Reaction Between Bone Components and ALP

Example 5-1. Evaluation of Affinity for Calcium Salts

The affinity of the NIR-Phos-1 and NIR-Phos-2 fluorescent probes for a calcium salt-containing scaffold was evaluated. As the scaffold, calcium carbonate (CC), calcium phosphate (CP), hydroxyapatite (HA), calcium perchlorate (CPC), calcium chloride (CCH) and calcium nitrate (CN) were used. The fluorescent probe and the scaffold were immersed in a PBS buffer and subjected to NIR fluorescence imaging. The result is shown in FIGS. 11A and 11B.

Figure 11A:
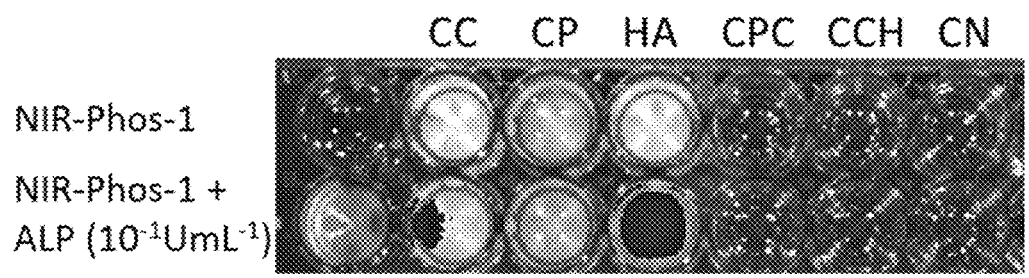
FIGS. 11A and 11B show a result of evaluating the affinity of a fluorescent probe for calcium salts.
Figure 11B:
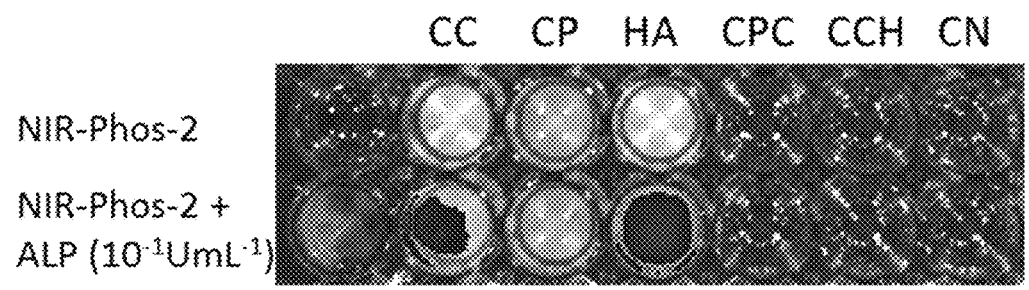

Referring to FIGS. 11A and 11B, it can be seen that the NIR-Phos-1 and NIR-Phos-2 fluorescent probes have higher affinity for hydroxyapatite (HA) particles as compared to the calcium salts including calcium carbonate (CC), calcium phosphate (CP), calcium perchlorate (CPC), calcium chloride (CCH) and calcium nitrate (CN).

Because the NIR-Phos-1 and NIR-Phos-2 fluorescent probes contain a phosphate group and a sulfonate group, it readily reacts with the $Ca^{2+}$ of hydroxyapatite (HA). When bound to HA, they react sensitively both in aqueous solutions or solid sates. Accordingly, it is expected that the NIR-Phos-1 and NIR-Phos-2 fluorescent probes can sensitively detect ALP in vivo by being fixed to the bone tissue.

Example 5-2. Evaluation of Bone Targeting Activity

Figure 12:
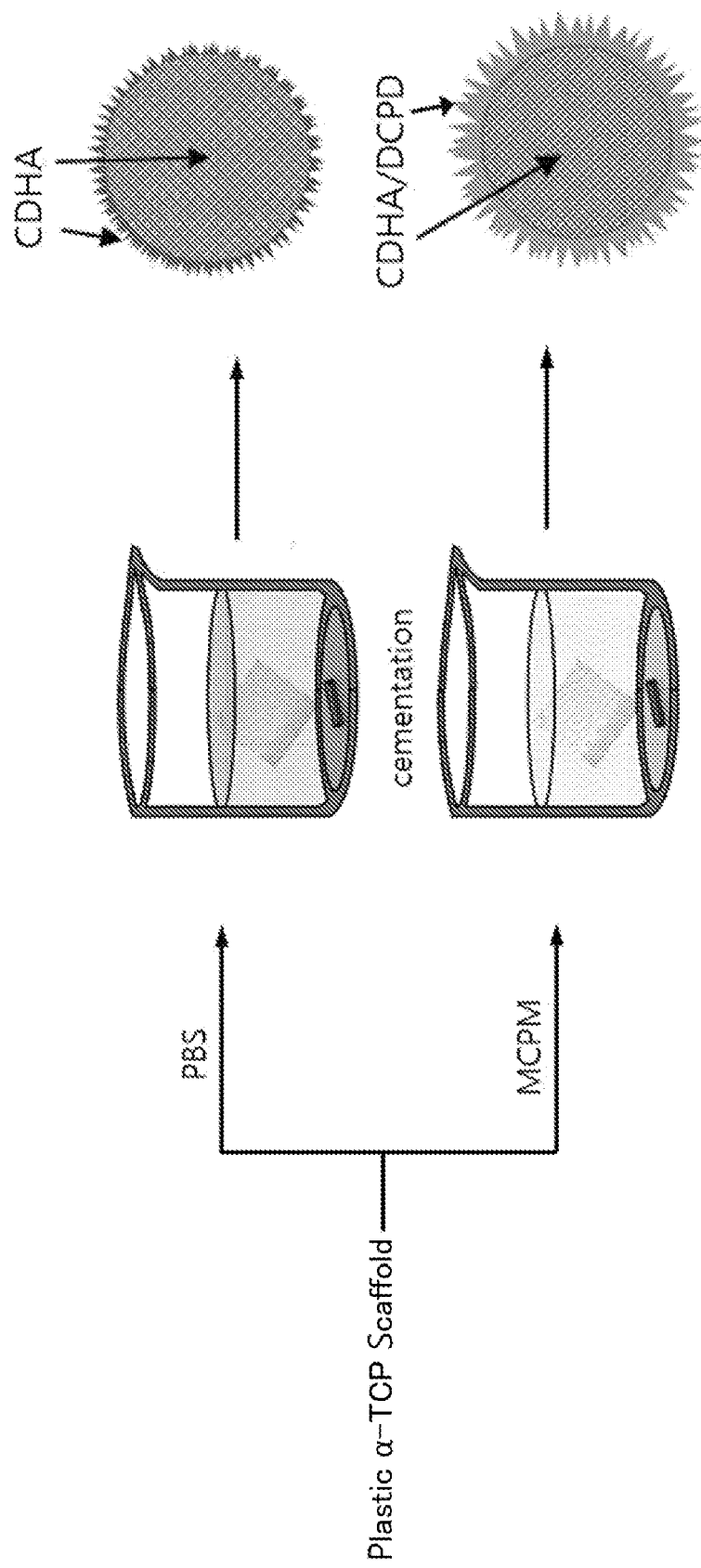
FIG. 12 shows a method for preparing a bone scaffold.

In order to evaluate the possibility of in-vivo bone targeting and ALP detection, the NIR-Phos-1 and NIR-Phos-2 fluorescent probes were bound to two types of calcium phosphate scaffolds (CDHA and CDHA/DCPD) and change in signals with time was measured by confocal imaging in the presence of ALP. Methods for preparing the calcium phosphate scaffolds are shown in FIG. 12.

The scaffold was prepared by 3D printing using α-TCP paste and a PED system. The 3D structure could be printed without deformation with sufficient flexibility, stability and workability. After the plastic α-TCP scaffold having a computer-controlled structure and pores was successfully prepared, the plastic scaffold was solidified in PBS and MCPM (monocalcium phosphate monohydrate) solutions. The XRD and SEM images of the prepared scaffold are shown in FIGS. 13A and 13B.

Figure 13A:
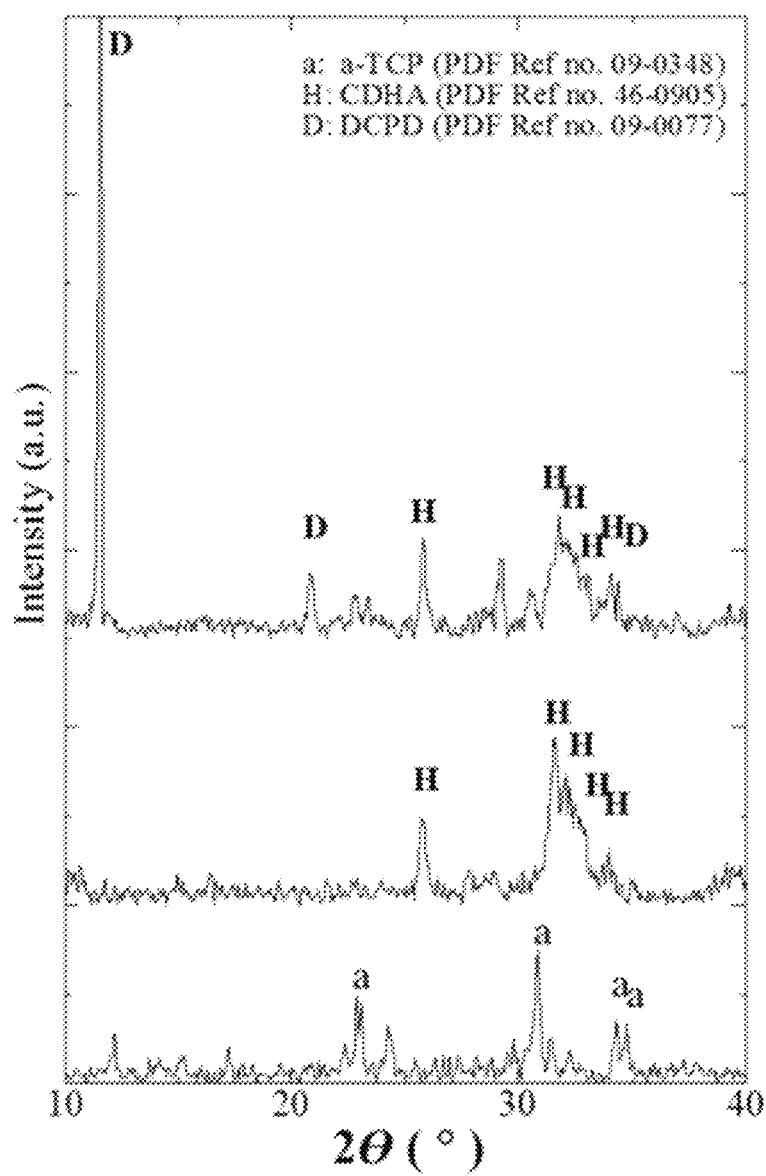
FIGS. 13A and 13B show the XRD and SEM images of a bone scaffold.

Referring to FIG. 13A, the XRD patterns show change in crystal structures due to the phase change of α-TCP to CDHA or CDHA/DCPD. When the scaffold was immersed in PBS, phase change occurred from α-TCP to CDHA due to hydrolysis of calcium phosphate. When the scaffold was immersed in MCPM, phase change occurred to DCPD on the scaffold surface and to CDHA inside the scaffold.

Figure 13B:
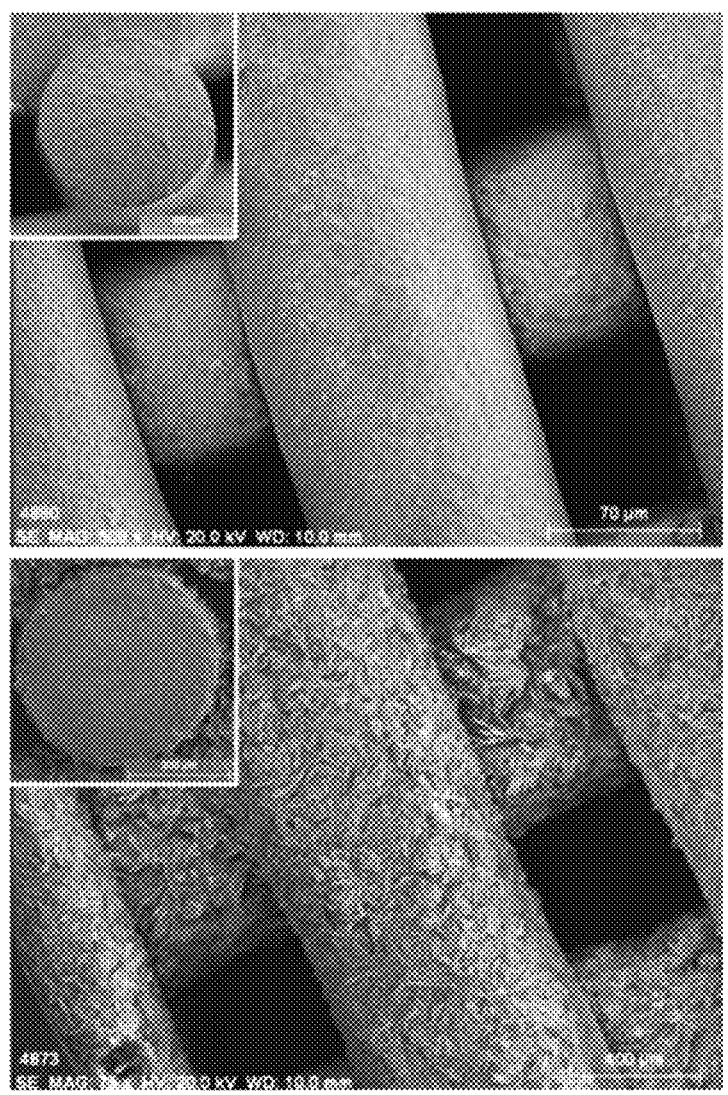

Referring to FIG. 13B, DCPD exhibited larger crystals and higher biodegradability than CDHA. The CDHA/DCPD scaffold showed a smaller surface area than the CDHA scaffold (top: CDHA, bottom: CDHA/DCPD).

Example 5-3. Evaluation of Affinity for Scaffold

Figure 14A:
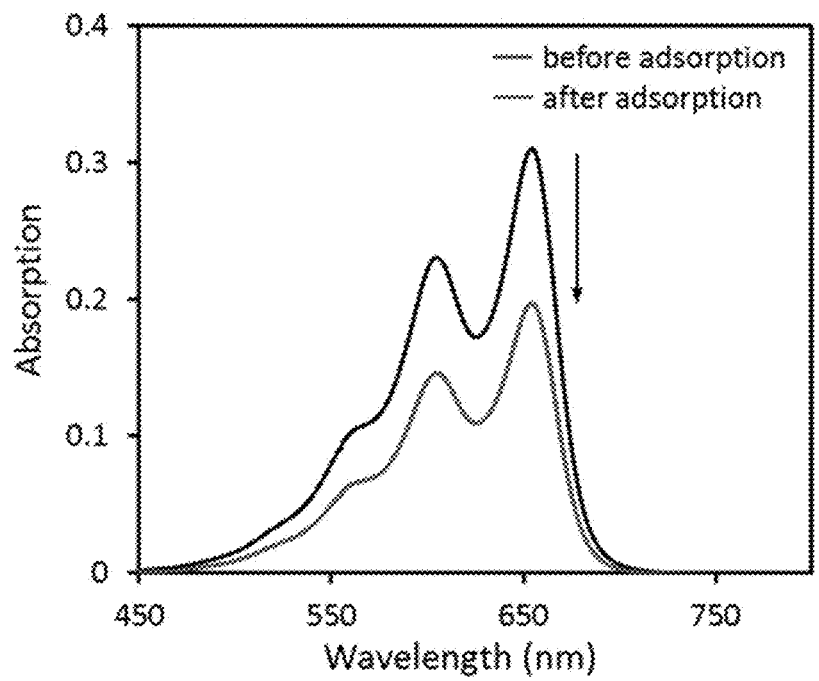
FIGS. 14A and 14B show the absorbance of a fluorescent probe-labeled scaffold (a: CDHA scaffold, b: CDHA/DCPD scaffold).
Figure 14B:
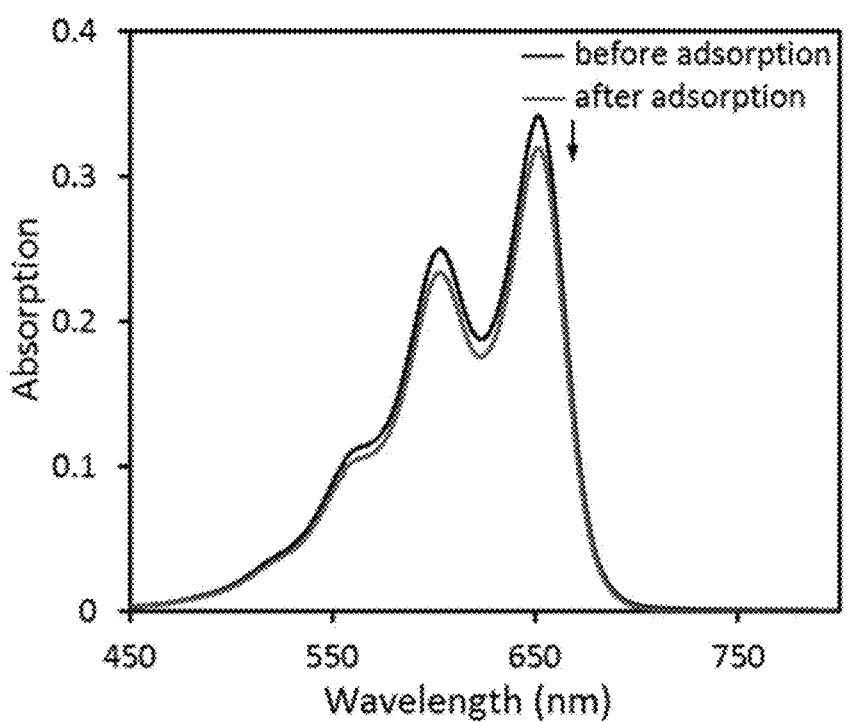

A NIR-Phos-1 fluorescent probe-labeled scaffold was prepared by using the strong affinity between the phosphate group of the NIR-Phos-1 fluorescent probe and the surface of the CDHA and CDHA/DCPD scaffolds and their effect on light absorption is shown in FIGS. 14A and 14B.

Referring to FIGS. 14A and 14B, it was confirmed that the light absorption by the NIR-Phos-1 fluorescent probe solution decreased after the adsorption, from 29.4% for the CDHA scaffold to 3.8% for the CDHA/DCPD scaffold. This may be due to the surface and morphological characteristics of the scaffold which affect the affinity for the phosphate group of the probe. To conclude, it was confirmed that the CDHA scaffold is more effective for labeling of the fluorescent probe than the CDHA/DCPD scaffold.

Example 5-4. Evaluation of Dephosphorylation of Fluorescent Probe

In order to confirm the dephosphorylation of the NIR-Phos-1 fluorescent probe on the scaffold by ALP, the scaffold was incubated in the ALP solution and light emission from the dephosphorylated fluorescent probe was measured. The fluorescent probe-labeled scaffold incubated in the absence of ALP was used as a control group. The result is shown in FIGS. 15A to 15C.

Figure 15A:
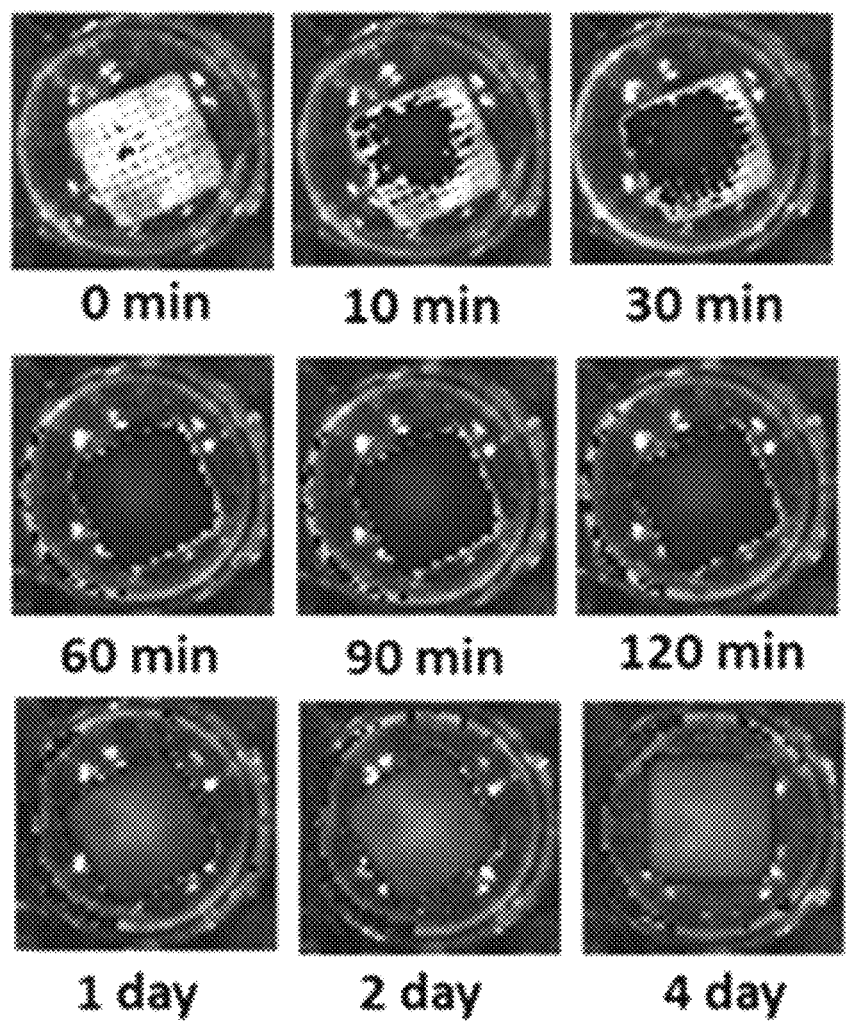
FIGS. 15A to 15C show a result of comparing the dephosphorylation of a fluorescent probe depending on scaffolds.
Figure 15B:
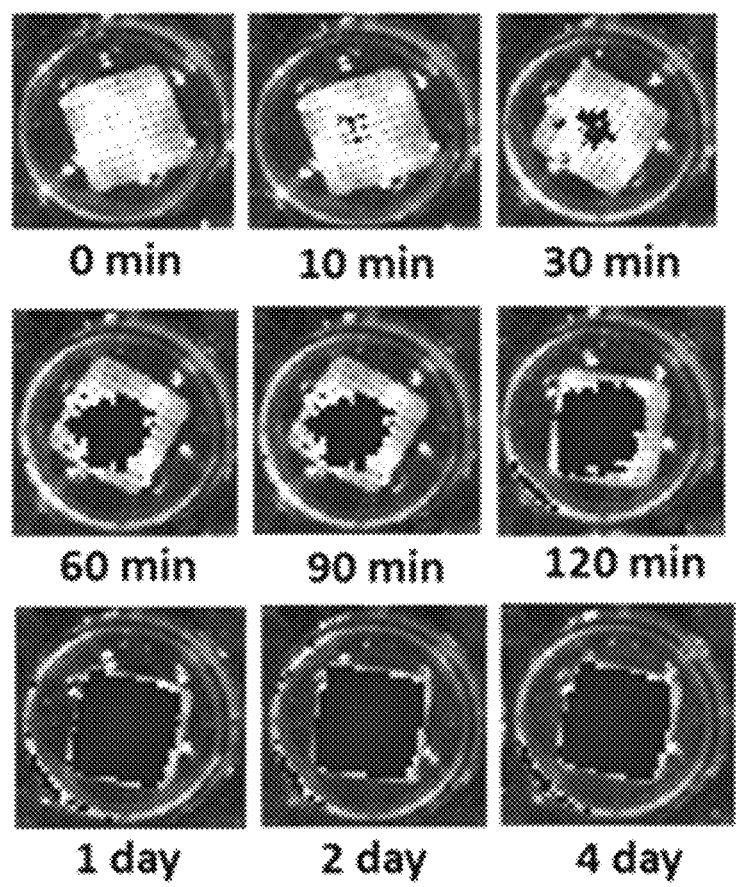
Figure 15C:
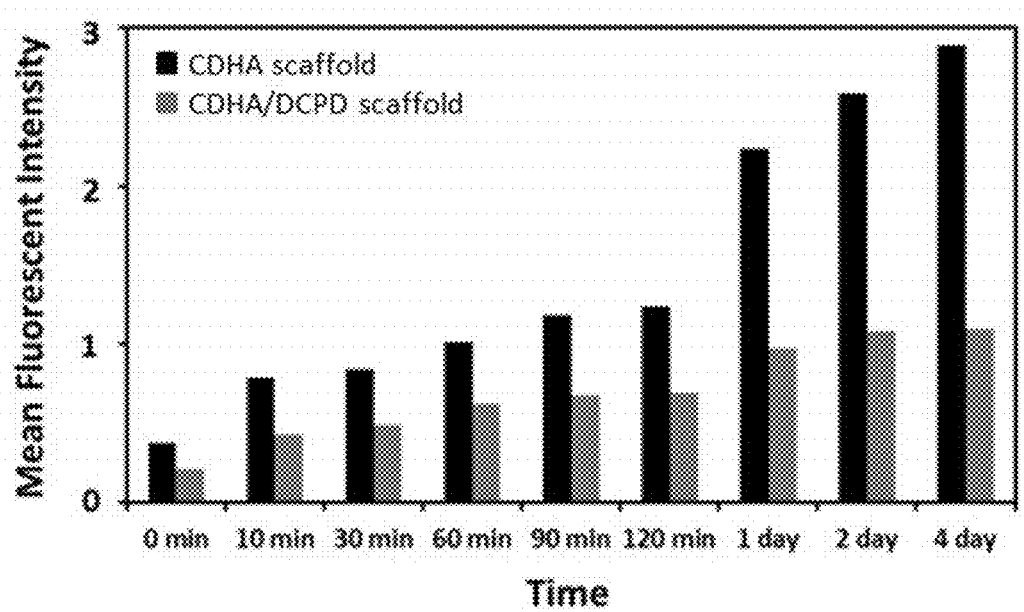

Referring to FIGS. 15A to 15C, in the early stage, a relatively strong fluorescence signal was observed due to the hydrolysis of ALP diffused in the CDHA matrix. However, the fluorescent probe showed significant difference in adsorption on the CDHA and CDHA/DCPD scaffolds. Fluorescence was enhanced for the CDHA scaffold.

Example 6. Investigation of Cytotoxicity with Time (CCK-8 Assay)

The cytotoxicity of the NIR-Phos-1 and NIR-Phos-2 fluorescent probes with time was evaluated (CCK-8 assays). The experiment was conducted while incubating HeLa cells and MC3T3-E1 cells with the fluorescent probes at concentrations of 0-100 μM for 1 hour. The result is shown in FIGS. 16A to 16D.

Figure 16A:
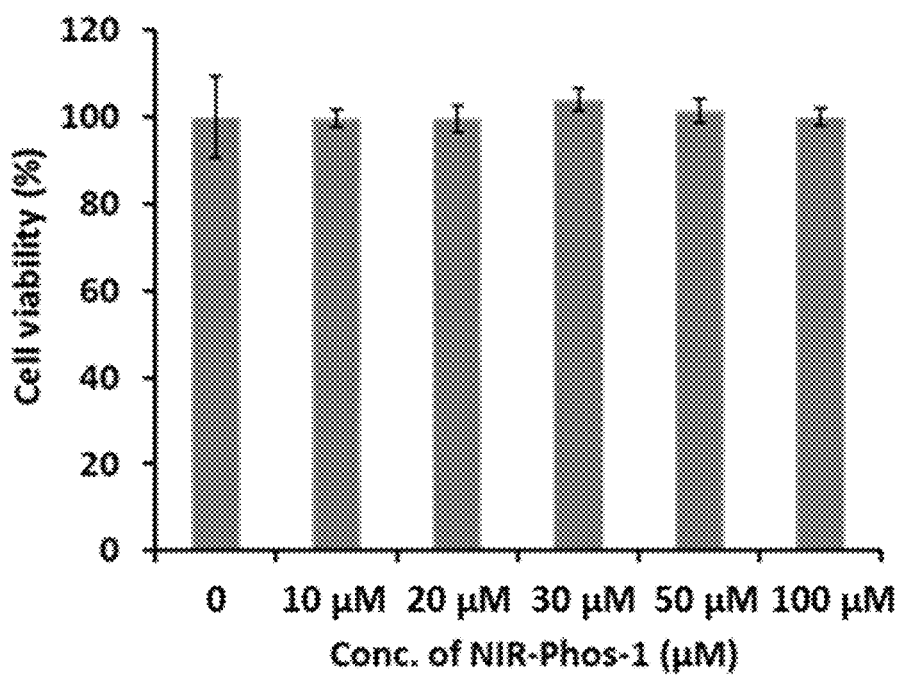
FIGS. 16A to 16D show a result of investigating the cytotoxicity of a fluorescent probe depending on concentration.
Figure 16B:
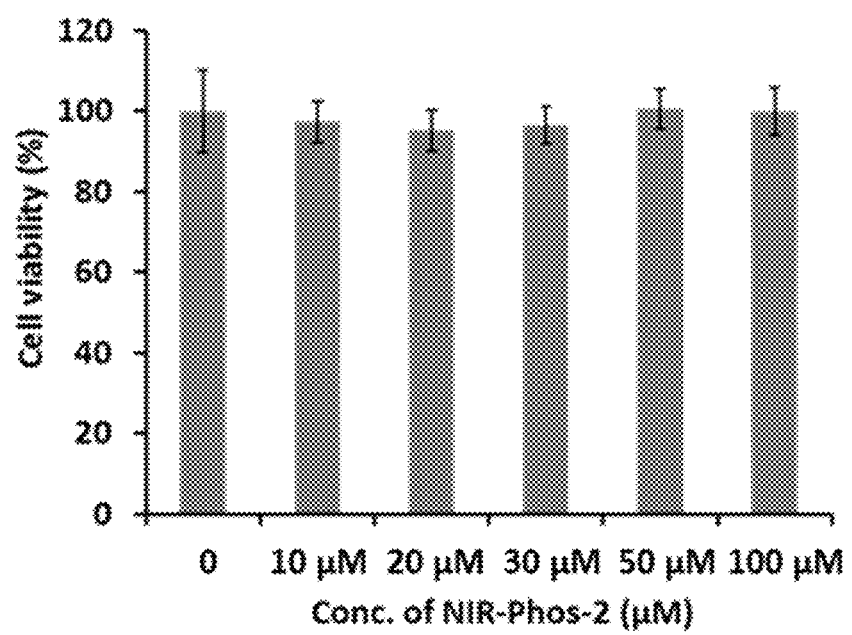
Figure 16C:
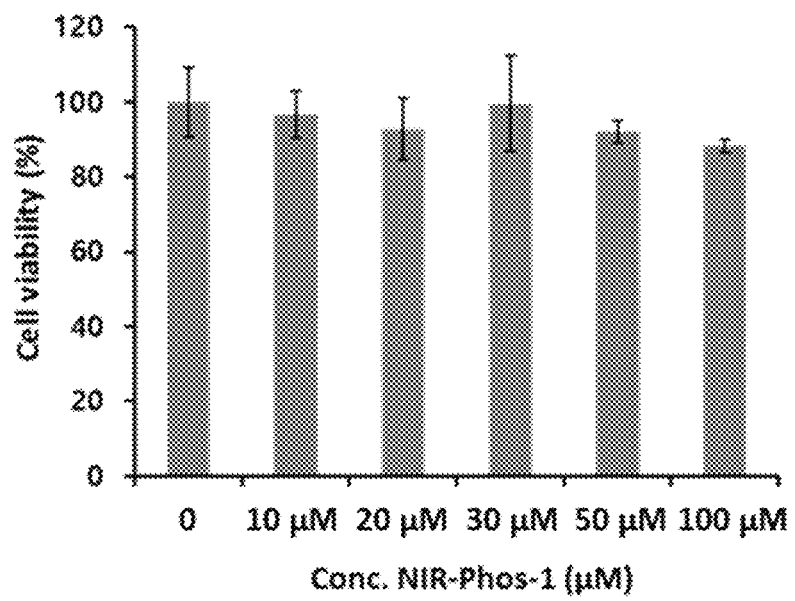
Figure 16D:
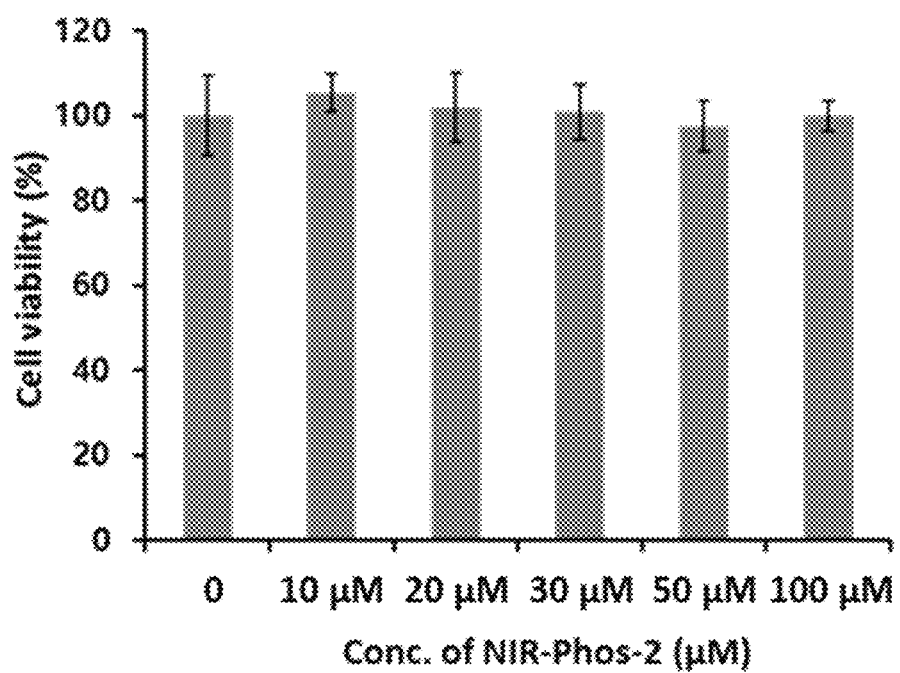

As seen from FIGS. 16A and 16D, the fluorescent probe of an embodiment of the present disclosure did not exhibit cytotoxicity because 95% of the HeLa cells and MC3T3-E1 cells survived.

Example 7. Monitoring of Intracellular Endogenous ALP Activity

Figure 17:
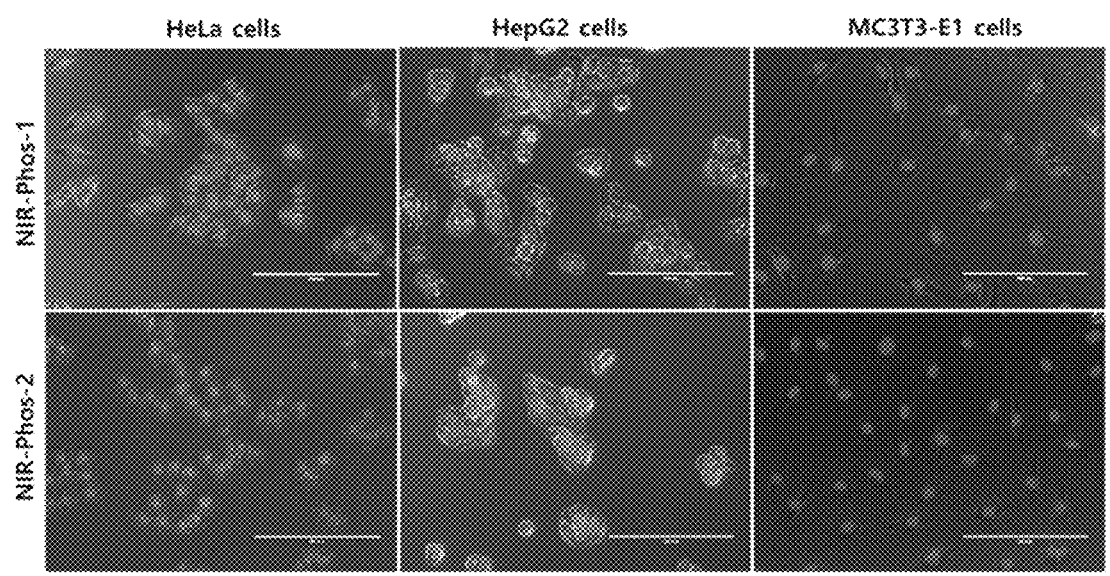
FIG. 17 shows a result of investigating the monitoring ability of a fluorescent probe for intracellular endogenous ALP activity.

The ability of monitoring endogenous ALP activity was evaluated by using HeLa cells and HepG2 cells as positive controls and MC3T3-E1 cells as a negative control. The result is shown in FIG. 17.

When the cells were incubated with 5 μM of the fluorescent probe, emission of red light at 655-794 nm was observed for the HeLa cells and HepG2 cells. Accordingly, the monitoring ability of the fluorescent probe of an embodiment of the present disclosure was confirmed.

Example 8. In-Vivo Experiment

Example 8-1. Detection of ALP In Vivo

After intravenously administering the NIR-Phos-1 fluorescent probe to a rat, the possibility of ALP detection was investigated. The result is shown in FIGS. 18A and 18B.

Figure 18A:
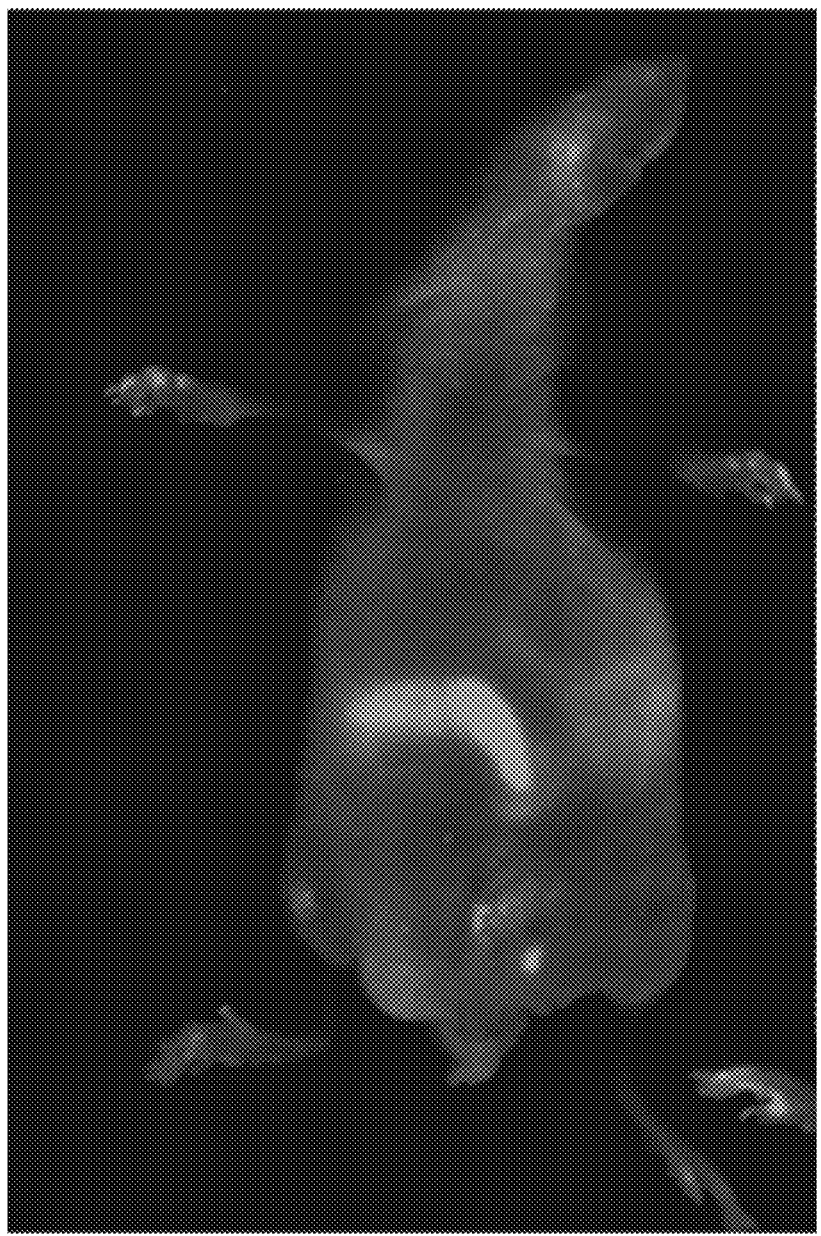
FIGS. 18A and 18B show fluorescence images of a rat into which a fluorescent probe is injected intravenously.
Figure 18B:
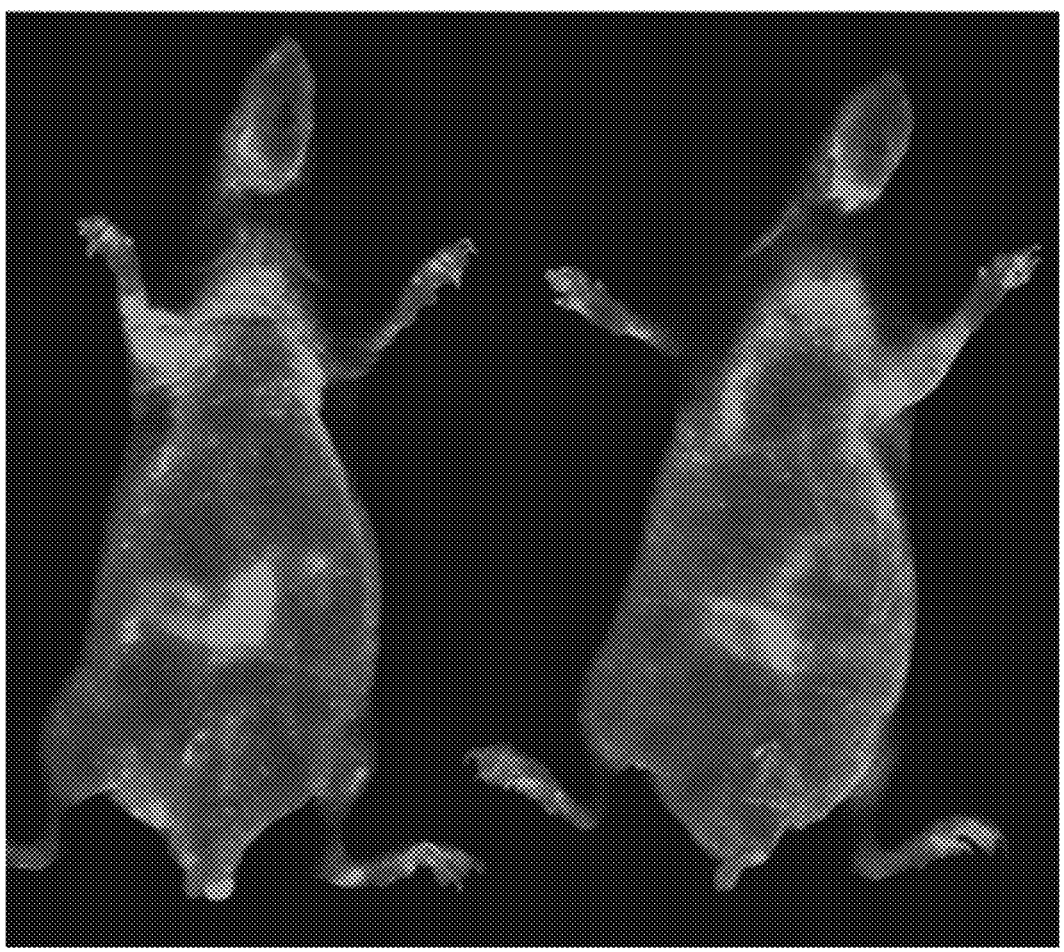

Referring to FIGS. 18A and 18B, the rat treated with the fluorescent probe showed very strong fluorescence intensities in normal bones of the rat, including the jawbone, leg bone and tailbone.

Example 8-2. Implantation of Fluorescent Probe-Containing Bone Scaffold

Figure 19:
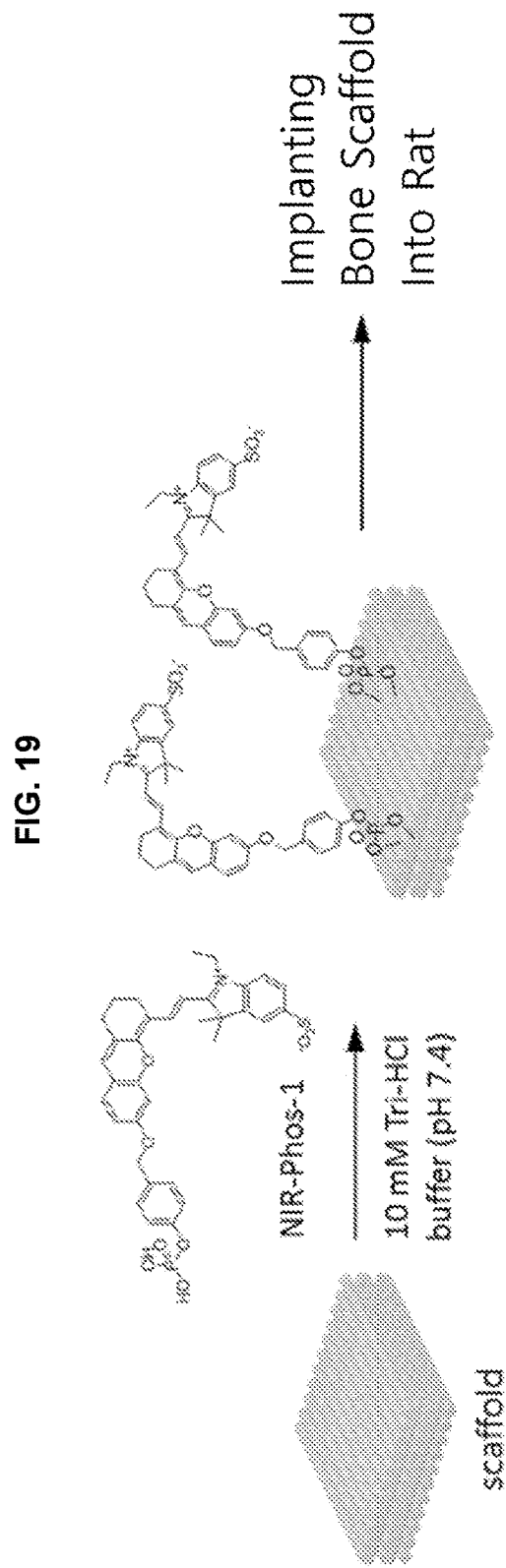
FIG. 19 shows implantation of a bone scaffold including a fluorescent probe into a rat.

After preparing a bone scaffold containing the NIR-Phos-1 fluorescent probe and implanting the same into a rat, fluorescence intensity was measured. As shown in FIG. 19, the bone scaffold was prepared by binding the NIR-Phos-1 fluorescent probe to the CDHA scaffold or the CDHA/DCPD scaffold and then implanted into a rat.

Figure 20A:
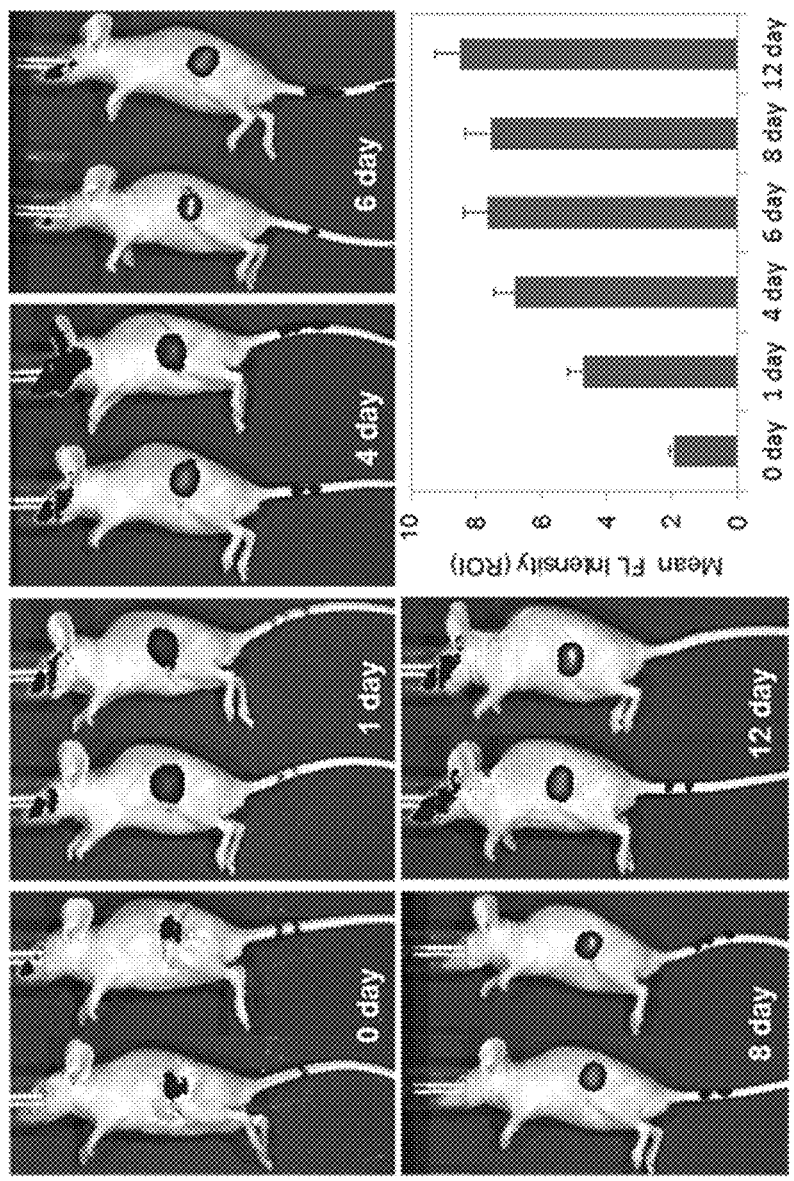
FIGS. 20A and 20B show fluorescence images of a rat into which a bone scaffold including a fluorescent probe is implanted (a: CDHA scaffold, b: CDHA/DCPD scaffold).
Figure 20B:
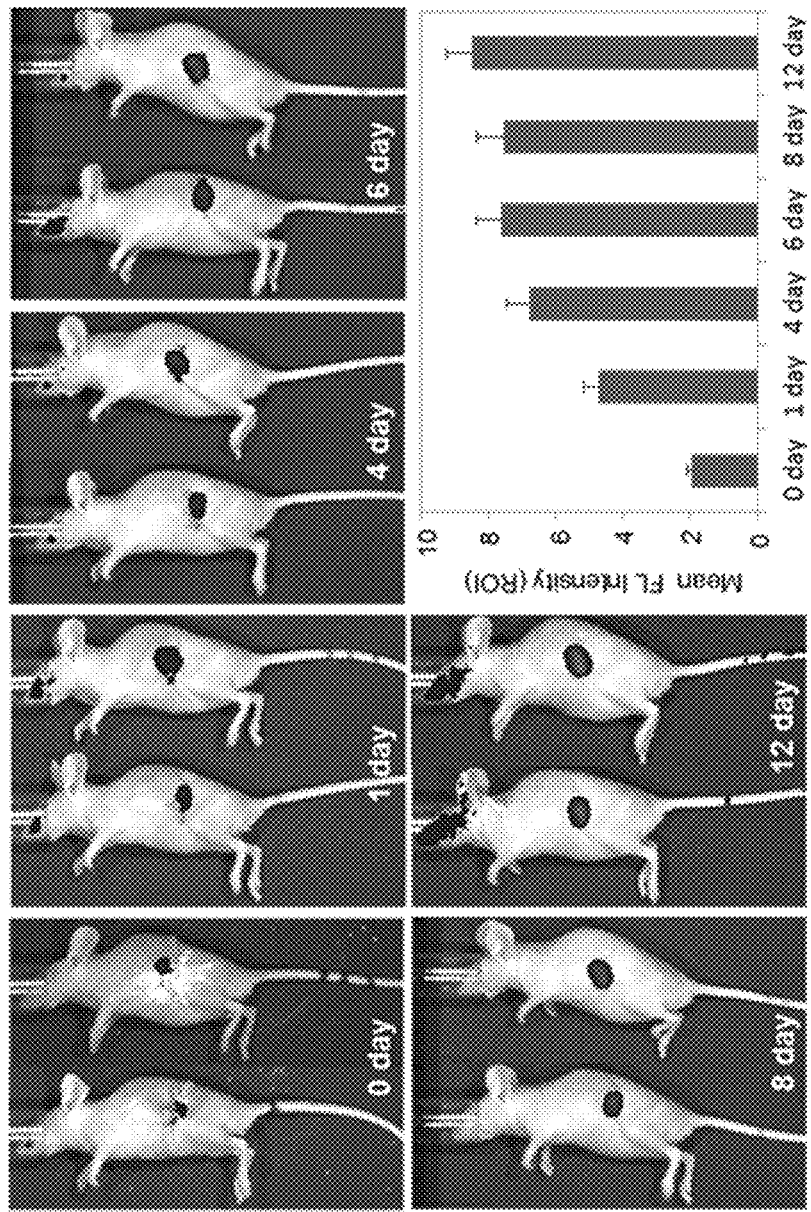

Then, fluorescence was observed on days 0, 1, 4, 6, 8 and 12 using the IVIS Lumina II imaging system (675 nm excitation filter, 695-770 nm emission filter). The result is shown in FIGS. 20A and 20B.

As a result, fluorescence was observed in the implanted area of the rat. Accordingly, it was confirmed that the fluorescent probe of the present disclosure can be used to monitor bone formation during the early osteogenic differentiation in real time.

Although the exemplary embodiments of the present invention have been disclosed for illustrative purposes, those skilled in the art will appreciate that various modifications, additions and substitutions are possible, without departing from the scope and spirit of the invention as disclosed in the accompanying claims.

What is claimed is:

1. A fluorescent probe for detecting ALP, represented by Chemical Formula 1:

[Chemical Formula 1]

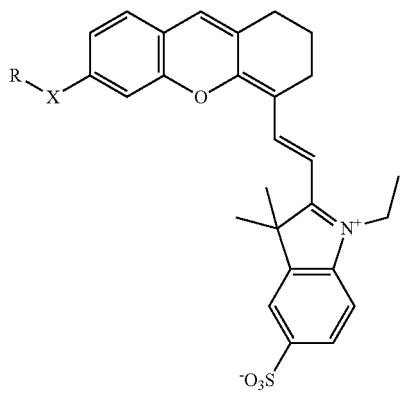

wherein X is O or NH; and
R is

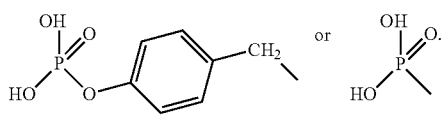

2. The fluorescent probe of claim 1, wherein the fluorescent probe fluoresces at 650 to 750 nm by reacting with ALP in vivo.

3. The fluorescent probe of claim 1, wherein the fluorescent probe is represented by Chemical Formula 2:

[Chemical Formula 2]

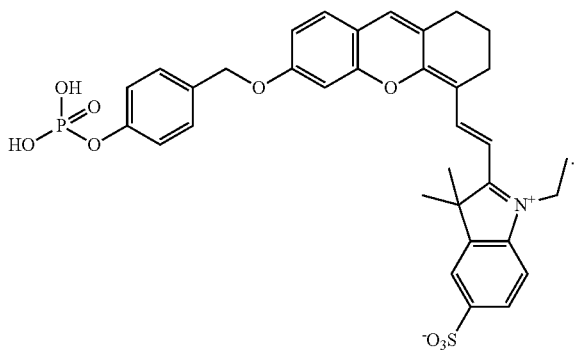

4. The fluorescent probe of claim 1, wherein the fluorescent probe is represented by Chemical Formula 3:

[Chemical Formula 3]

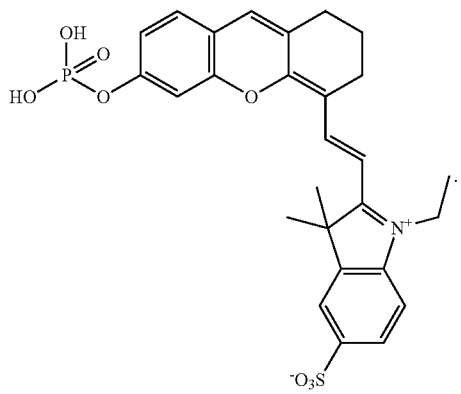

5. The fluorescent probe of claim 1, wherein X is O.
6. The fluorescent probe of claim 1, wherein X is NH.
7. The fluorescent probe of claim 1, wherein R is

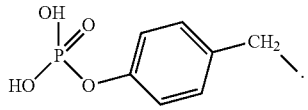

8. The fluorescent probe of claim 1, wherein R is or

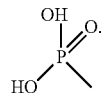

9. A bone scaffold comprising the fluorescent probe of claim 1.
10. A method for preparing a fluorescent probe for detecting ALP, the method comprising:
obtaining a compound represented by Chemical Formula 6 by reacting a compound represented by Chemical Formula 4 with a compound represented by Chemical Formula 5;
obtaining a compound represented by Chemical Formula 8 by reacting the compound represented by Chemical Formula 6 with a compound represented by Chemical Formula 7; and obtaining a compound represented by Chemical Formula 2 by reacting the compound represented by Chemical Formula 8 with a silane compound:

[Chemical Formula 4]

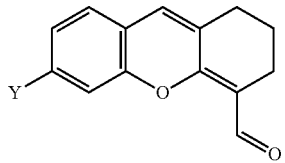

wherein Y is OH or NH₂;

[Chemical Formula 5]

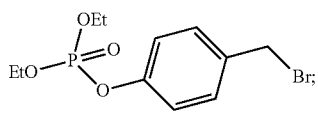

[Chemical Formula 6]

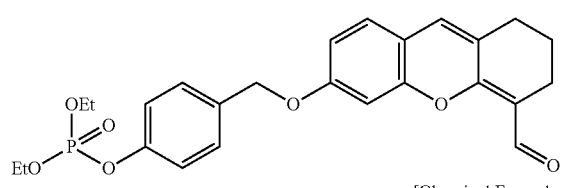

[Chemical Formula 7]

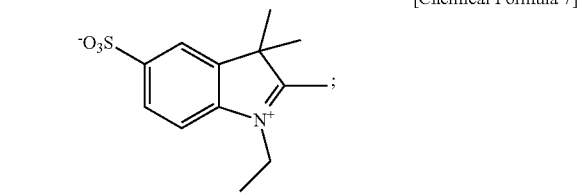

[Chemical Formula 8]

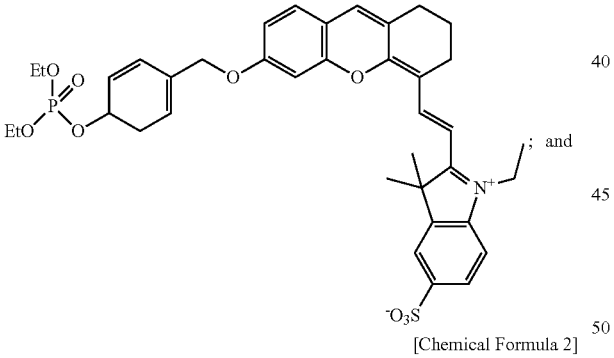
; and

[Chemical Formula 2]

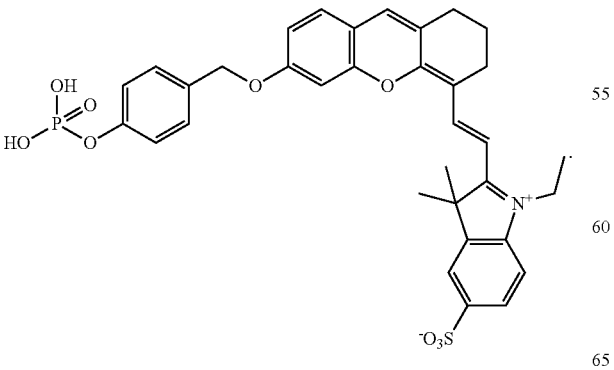

11. The method of claim 10, wherein the silane compound is iodotrimethylsilane.

12. A method for preparing a fluorescent probe for detecting ALP, the method comprising:

obtaining a compound represented by Chemical Formula 10 by reacting a compound represented by Chemical Formula 4 with a compound represented by Chemical Formula 9;

obtaining a compound represented by Chemical Formula 11 by reacting the compound represented by Chemical Formula 10 with a compound represented by Chemical Formula 7; and obtaining a compound represented by Chemical Formula 3 by reacting the compound represented by Chemical Formula 11 with a silane compound:

[Chemical Formula 4]

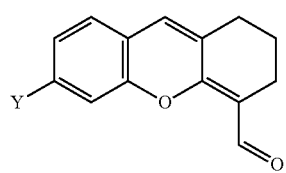

wherein Y is OH or NH₂;

[Chemical Formula 9]

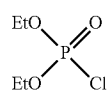

[Chemical Formula 10]

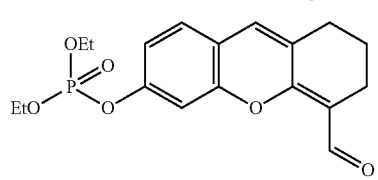

[Chemical Formula 7]

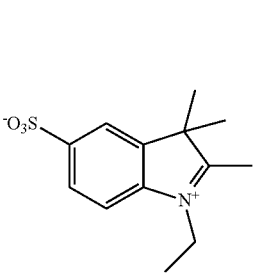

[Chemical Formula 11]

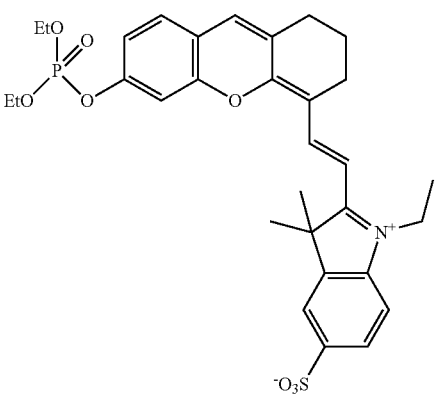

-continued
[Chemical Formula 3]
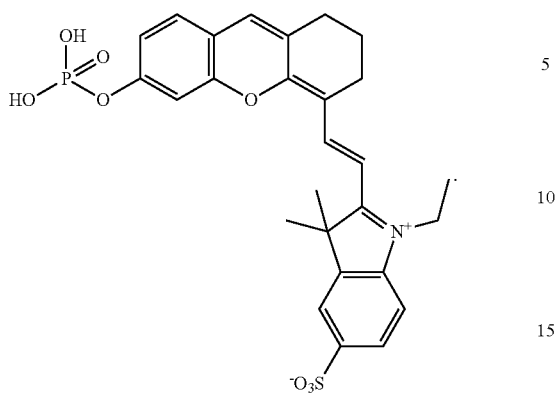
13. The method of claim 12, wherein the silane compound is iodotrimethylsilane.